United States Patent
Lee et al.

(10) Patent No.: US 9,636,075 B2
(45) Date of Patent: May 2, 2017

(54) SIMULATION-BASED ESTIMATION OF ELASTICITY PARAMETERS AND USE OF SAME FOR NON-INVASIVE CANCER DETECTION AND CANCER STAGING

(71) Applicant: The University of North Carolina at Chapel Hill, Chapel Hill, NC (US)

(72) Inventors: Huai-Ping Lee, Plantation, FL (US); Mark Stephen Foskey, Chapel Hill, NC (US); Marc Niethammer, Carrboro, NC (US); Ming Lin, Chapel Hill, NC (US)

(73) Assignee: THE UNIVERSITY OF NORTH CAROLINA AT CHAPEL HILL, Chapel Hill, NC (US)

(*) Notice: Subject to any disclaimer, the term of this patent is extended or adjusted under 35 U.S.C. 154(b) by 254 days.

(21) Appl. No.: 14/420,239

(22) PCT Filed: Aug. 6, 2013

(86) PCT No.: PCT/US2013/053803
§ 371 (c)(1),
(2) Date: Feb. 6, 2015

(87) PCT Pub. No.: WO2014/025791
PCT Pub. Date: Feb. 13, 2014

(65) Prior Publication Data
US 2015/0216496 A1    Aug. 6, 2015

Related U.S. Application Data

(60) Provisional application No. 61/680,116, filed on Aug. 6, 2012.

(51) Int. Cl.
*A61B 6/06*    (2006.01)
*A61B 6/00*    (2006.01)
(Continued)

(52) U.S. Cl.
CPC ............ *A61B 6/5217* (2013.01); *A61B 6/032* (2013.01); *A61B 6/466* (2013.01); *A61B 6/50* (2013.01);
(Continued)

(58) Field of Classification Search
None
See application file for complete search history.

(56) References Cited

U.S. PATENT DOCUMENTS

2002/0137014 A1    9/2002    Anderson et al.
2007/0239409 A1    10/2007    Alan
(Continued)

OTHER PUBLICATIONS

Notification of Transmittal of the International Search Report and the Written Opinion of the International Searching Authority, or the Declaration for International Application No. PCT/US2013/053803 (Nov. 1, 2013).
(Continued)

*Primary Examiner* — Joseph M Santos Rodriguez
(74) *Attorney, Agent, or Firm* — Jenkins, Wilson, Taylor & Hunt, P.A.

(57) ABSTRACT

Simulation-based estimation of elasticity parameters and use of same for non-invasive cancer detection and cancer staging are disclosed. According to one aspect, a method for simulation-based estimation of elasticity parameters includes constructing a 3D model of an object comprising biological tissue, the model having a first shape and an elasticity value. A simulation iteration is then performed, which includes simulating the application of an external force to the model, causing the model to have a second shape, measuring the difference between the second shape and a target shape, and determining whether the measured difference between the second shape and the target shape is within a threshold of error. If the measured difference is not within the threshold of error, the process performs additional
(Continued)

iterations using adjusted elasticity or force values until the measured difference is within the threshold of error, at which time the final elasticity and force values are reported. In one embodiment, the elasticity value is mapped to a diagnostic parameter, such as an indication of the possibility, presence, or stage of cancer.

13 Claims, 20 Drawing Sheets

(51) Int. Cl.
*G06T 19/20* (2011.01)
*G06T 7/00* (2017.01)
*A61B 6/03* (2006.01)
*G06T 15/00* (2011.01)

(52) U.S. Cl.
CPC .......... *G06T 7/0012* (2013.01); *G06T 7/0032* (2013.01); *G06T 15/00* (2013.01); *G06T 19/20* (2013.01); *G06T 2207/10081* (2013.01); *G06T 2207/30081* (2013.01); *G06T 2210/41* (2013.01); *G06T 2219/2021* (2013.01)

(56) References Cited

U.S. PATENT DOCUMENTS

2010/0305928 A1 12/2010 Cohen et al.
2010/0305929 A1 12/2010 Andersen et al.
2012/0165702 A1 6/2012 Hauck

OTHER PUBLICATIONS

Alterovitz et al., "Registration of MR Prostate Images With Biomechanical Modeling and Nonlinear Parameter Estimation:" Medical Physics, vol. 33, No. 2, pp. 446-454 (2006).
Balay et al., "Efficient Management of Parallelism in Object-Oriented Numerical Software Libraries," Modern Software Tools in Scientific Computing, pp. 1-29, (1997).
Balocco et al., "Towards Regional Elastography of Intracranial Aneurysms," Medical Image Computing and Computer-Assisted Intervention, vol. 11, pp. 131-138 (2008).
Barbic et al., "Deformable Object Animation Using Reduced Optimal Control." ACM Transactions on Graphics—Preceedings of ACM SIGGRAPH 2009, vol. 28, No. 3, Article 53, pp. 53:1-53:9, http://portal.acm.org/citation.cfm?doid=1531326.1531359 (Aug. 2009).
Becker et al., "Robust and Efficient Estimation of Elasticity Parameters Using the Linear Finite Element Method," in Proceedings of Simulation and Visualization, pp. 1-14, (2007).
Bergou et al., "TRACKS: Toward Directable Thin Shells," in ACM Transactions on Graphics, vol. 26, No. 3, Article 50, pp. 50-1-50-10, http://portal.acm.org/citation.cfm?id=1275808.1276439&coll=portal&dl=ACM&CFID=92920094&CFTOKEN=78895682 (Jul. 2007).
Bharatha et al., "Evaluation of three-dimensional finite element-based deformable registration of pre- and and intraoperative prostate imaging," Medical Physics, vol. 28, No. 12, p. 2551-2560 (2001).
Bhat et al., "Estimating Cloth Simulation Parameters From Video." In Proceedings of the ACM SIGGRAPH/Eurographics Symposium on Computer Animation, Eurographics Association, Switzerland, pp. 37-51 (2003).
Bickel et al., "Capture and Modeling of Non-Linear Heterogeneous Soft Tissue," in ACM Transactions on Graphics, vol. 28, No. 3, Article 89, pp. 89:1-89:9, http://portal.acm.org/citation.cfm?id=1531395 (Aug. 2009).
Bickel et al., "Design and Fabrication of Materials With Desired Deformation Behavior," in ACM Transactions on Graphics, vol. 29, No. 4, Article 63, pp. 63:1-63:9, http://portal.acm.org/citation.cfm?id=1833349.1778800&coll=GUIDE&dl=GUIDE&CFID=107466681&CFTOKEN=52303178 (Jul. 2010).
Cash et al., "Compensating for Intraoperative Soft-Tissue Deformations Using Incomplete Surface Data and Finite Elements," IEEE Transactions on Medical Imaging, vol. 24, No. 11, pp. 1479-1491 (Nov. 2005).
Chopra et al., "In Vivo MR Elastography of the Prostate Gland Using a Transurethral Actuator," Magnetic Resonance in Medicine, vol. 62, No. 3, pp. 665-671 (2009).
Courtis et al., "Detecting Mechanical Abnormalities in Prostate Tissue Using FE-Based Image Registration," in MICCAI 2007, Part II, LNCS 4792, pp. 244-251 (2007).
Crouch et al., "Automated Finite-Element Analysis for Deformable Registration of Prostate Images," IEEE Transactions on Medical Imaging, vol. 26, No. 10, pp. 1379-1390 (Oct. 2007).
Egorov et al., "Prostate Mechanical Imaging: 3-D Image Composition and Feature Calculations," IEEE Transactions on Medical Imaging, vol. 25, No. 10, pp. 1329-1340 (Oct. 2006).
Eskandari et al., "Real-time Solution of the Finite Element Inverse Problem of Viscoelasticity," Inverse Problems, vol. 27, pp. 1-16 (Aug. 2011).
Ferrant et al., "3D Image Matching Using a Finite Element Based Elastic Deformation Model," in MICCAI, pp. 1-8 (1999).
Ferrant et al., "Registration of 3D Intraoperative MR Images of the Brain Using a Finite Element Biomechanical Model," in MICCAI, pp. 1-10 (2000).
Foskey et al., "Large Deformation Three-Dimensional Image Registration in Image-Guided Radiation Therapy." Physics in Medicine and Biology, vol. 50, pp. 5869-5892 (2005).
Fu et al., "Non-Invasive Quantitative Reconstruction of Tissue Elasticity Using an Iterative Forward Approach," Physics in Medicine and Biology, vol. 45(6), pp. 1495-1509 (2000).
Han et al., "Development of Patient-Specific Biomechanical Models for Predicting Large Breast Deformation," Physics in Medicine and Biology, vol. 57, pp. 455-472 (Jan. 2012).
Hensel et al., "Development of Multiorgan Finite Element-Based Prostate Deformation Model Enabling Registration of Endorectal Coil Magnetic Resonance Imaging for Radiotherapy Planning," International Journal of Radiation Oncology Biol. Phys., vol. 68, No. 5, pp. 1522-1528 (2007).
Holden, "A Review of Geometric Transformations for Nonrigid Body Registration," IEEE Transactions on Medical Imaging, vol. 27, No. 1, pp. 111-128 (Jan. 2008).
Kallel et al., "Tissue Elasticity Reconstruction Using Linear Perturbation Method," IEEE Transactions on Medical Imaging, vol. 15, No. 3, pp. 299-313 (Jun. 1996).
Kauer et al., "Inverse Finite Element Characterization of Soft Tissues," Medical Image Analysis, vol. 6, pp. 275-287 (Sep. 2002).
Krouskop et al., "Elastic Moduli of Breast and Prostate Tissues Under Compression," Ultrasonic Imaging, vol. 20, No. 4, pp. 260-274 (1998).
Krysl et al., "Dimensional Model Reduction in Non-Linear Finite Element Dynamics of Solids and Structures," International Journal for Numerical Methods in Engineering, vol. 51(4), pp. 479-504, http://onlinelibrary.wiley.com/doi/10.1002/rune.167/abstract (2001).
Lee et al., "Physically-Based Deformable Image Registration With Material Property and Boundary Condition Estimation," in Proceedings of the IEEE International Conference on Biomedical Imaging, pp. 532-535, http://portal.acm.org/citation.cfm?id=1855963.1856099 (2010).
Lindop et al., "3D Elastography Using Freehand Ultrasound," Ultrasound in Medicine & Biology, vol. 32, No. 4, pp. 529-545 (Apr. 2006).
Maintz et al., "A Survey of Medical Image Registration," Medical Image Analysis, vol. 2, No. 1, pp. 1-36 (1998).
Manduca et al., "Magnetic Resonance Elastography: Non-Invasive Mapping of Tissue Elasticity," Medical Image Analysis, vol. 5, pp. 237-254 (Dec. 2001).
McNamara et al., "Fluid Control Using the Adjoint Method." ACM Transactions on Graphics, vol. 23(3), pp. 449-456, http://portal.acm.org/citation.cfm?id=1015706.1015744 (2004).

(56) References Cited

OTHER PUBLICATIONS

Moireau et al., "Joint State and Parameter Estimation for Distributed Mechanical Systems," Computer Methods in Applied Mechanics and Engineering, vol. 197, pp. 659-677 (Jan. 2008).
Muthupillai et al., "Magnetic Resonance Elastography," Nature Medicine, vol. 2, No. 5, pp. 601-603 (May 1996).
Nealen et al., "Physically Based Deformable Models in Computer Graphics," Computer Graphics Forum, vol. 25, No. 4, pp. 809-836 (2006).
Ophir et al., "Elastography: Ultrasonic Estimation and Imaging of the Elastic Properties of Tissues," Proceedings of the Institution of Mechanical Engineers, Part H: Journal of Engineering in Medicine, vol. 213, pp. 203-233 (Jan. 1999).
Rivaz et al., "Ultrasound Elastography: A Dynamic Programming Approach," IEEE Transactions on Medical Imaging, vol. 27, No. 10, pp. 1373-1377 (Oct. 2008).
Salcudean et al., "Viscoelasticity Modeling of the Prostate Region Using Vibro-elastography," in Medical Image Computing and Computer-Assisted Intervention—MICCAI, vol. 4190, pp. 389-396 (2006).
Schnur et al., "An Inverse Method for Determining Elastic Material Properties and a Material Interface," International Journal for Numerical Methods in Engineering, vol. 33, No. 10, pp. 2039-2057 (1992).
Sermesant et al., "Cardiac Function Estimation from MRI Using a Heart Model and Data Assimilation: Advances and Difficulties," Medical Image Analysis, vol. 10, No. 4, pp. 642-656 (2006).
Shewchuk, "Triangle: Engineering a 2D Quality Mesh Generator and Delaunay Triangulator," in Applied Computational Geometry Towards Geometric Engineering, vol. 1148, pp. 1-10, http://www.springerlink.com/content/w164563587465326/ (1996).
Skovoroda et al., "Tissue Elasticity Reconstruction Based on Ultrasonic Displacement and Strain Images," IEEE Transactions on Ultrasonics, Ferroelectrics, and Frequency Control, vol. 42, No. 4, pp. 747-765 (Jul. 1995).
Syllebranque et al., "Estimation of Mechanical Parameters of Deformable Solids from Videos," The Visual Computer, vol. 24, No. 11, pp. 963-972 (2008).
Tanner et al., "Factors Influencing the Accuracy of Biomechanical Breast Models," Medical Physics, vol. 33, No. 6, pp. 1758-1769 (Jun. 2006).
Taylor et al., "Real-Time Surgical Simulation Using Reduced Order Finite Element Analysis," MICCAI 2010, Part II, LNCS 6362, pp. 388-395 http://www.ncbi.nlm.nih.gov/pubmed/20879339, PMTD: 20879339, (2010).
Igarashi et al., "As-Rigid-As-Possible Shape Manipulation." ACM Transactions on Graphics, vol. 24(3), pp. 1134-1141, http://doi.acm.org/10.1145/1073204.1073323, (2005).
Thirion, "Image Matching as a Diffusion Process: An Analogy With Maxwell's Demons," Medical Image Analysis, vol. 2, No. 3, pp. 243-260 (1998).
Treuille et al., "Keyframe Control of Smoke Simulations," in ACM SIGGRAPH 2003 Papers, pp. 716-723, http://portal.acm.org/citation.cfm?id=1201775.882337&coll=portal&dl=ACM&CFID=92920094&CFTOKEN=78895682 (2003).
Washington et al., "Modality Independent Elastography (MIE): A New Approach to Elasticity Imaging," IEEE Transactions on Medical Imaging, vol. 23, No. 9, pp. 1117-1128 (Sep. 2004).
Weng et al., "2D Shape Deformation Using Nonlinear Least Sqaures Optimization," The Visual Computer, vol. 22(9-11), pp. 653-660, http://www.springerlink.com/content/8hwv2183455t232v/ (2006).
Yang et al., "Shape Deformation with Tunable Stiffness," The Visual Computer, vol. 24(7-9), pp. 495-503, http://www.springerlink.com/content/q22t771352785451/ (2008).
Yoo et al., "Engineering and Algorithm Design for an Image Processing API: A Technical Report on ITK—The Insight Toolkit," Studies in Health Technology and Informatics, vol. 85, pp. 586-592 (2002).
Yushkevich et al., "User-Guided 3D Active Contour Segmentation of Anatomical Structures: Significantly Improved Efficiency and Reliability," NeuroImage, vol. 31, pp. 1116-1128 (Jul. 2006).
Zhu et al., "A Finite-Element Approach for Young's Modulus Reconstruction," IEEE Transactions on Medical Imaging, vol. 22, No. 7, pp. 890-901 (Jul. 2003).
Zienkiewicz et al., "The Finite Element Method: Its Basis and Fundamentals," Sixth Edition (Dec. 2005).
Wittek et al. "Patient-Specific Model of Brain Deformation: Application to Medical Image Registration," Journal of Biomechanics, vol. 40, No. 4, pp. 919-929 (2007).

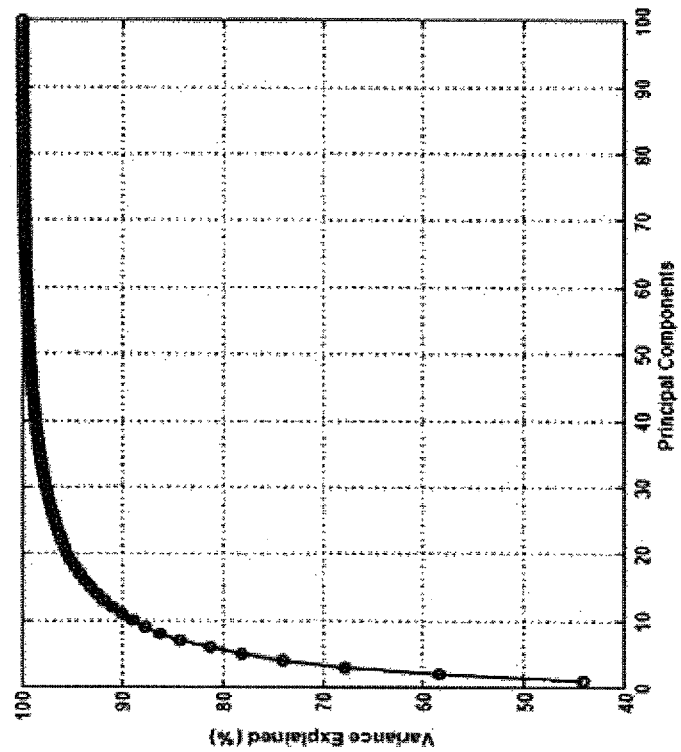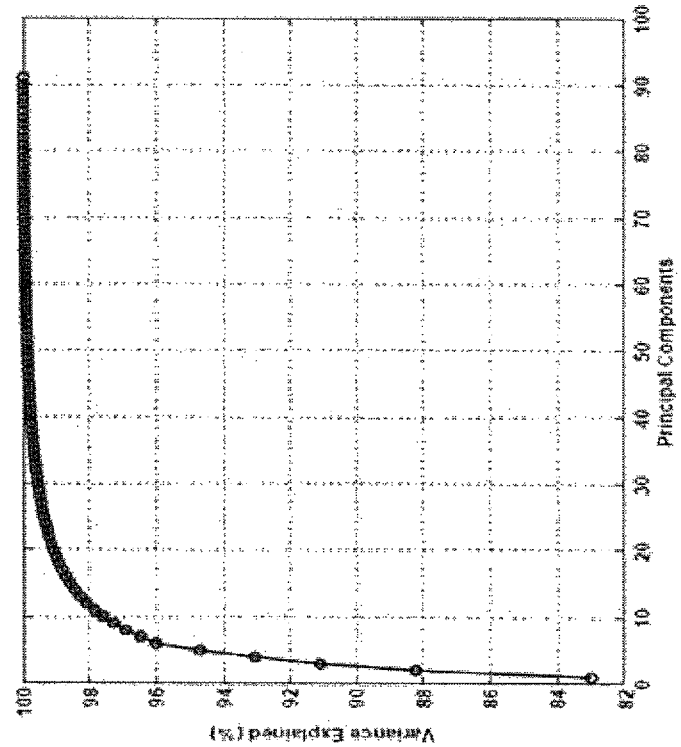
FIG. 14

SIMULATION-BASED ESTIMATION OF ELASTICITY PARAMETERS AND USE OF SAME FOR NON-INVASIVE CANCER DETECTION AND CANCER STAGING

PRIORITY CLAIM

This application claims the benefit of U.S. Provisional Patent Application Ser. No. 61/680,116, filed Aug. 6, 2012; the disclosure of which is incorporated herein by reference in its entirety.

GOVERNMENT INTEREST

This invention was made with government support under Grant No. W911NF-06-1-0355 awarded by the U.S. Army Research Office and Grant No. R01 RR018615 awarded by the National Center for Research Resources and the National Cancer Institute. The U.S. Government has certain rights in the invention.

TECHNICAL FIELD

The subject matter described herein relates to methods and systems for characterization of biological tissue elasticity using non-invasive means. More specifically, the subject matter described herein relates to simulation-based estimation of elasticity parameters, which may be used for non-invasive cancer detection and cancer staging.

BACKGROUND

Estimation of tissue stiffness is an important means of noninvasive cancer detection. Existing elasticity reconstruction methods usually depend on a dense displacement field (given by ultrasound or MR images) and known external forces. Many imaging modalities, however, cannot provide details within an organ and therefore cannot provide such a displacement field. Furthermore, force exertion and measurement can be difficult for some internal organs, making boundary forces another missing parameter.

Material property estimation has been an important topic in noninvasive cancer diagnosis, since cancerous tissues tend to be stiffer than normal tissues. Traditional physical examination methods, such as palpation, are limited to detecting lesions close to the skin, and reproducible measurements are hard to achieve. With the advance of medical imaging technologies, it becomes possible to quantitatively study the material properties using noninvasive procedures.

Computer vision methods in combination with force or pressure sensing devices have been proposed to find material properties of tissues [1], [2]. These methods require a controlled environment in order to capture the video and force (pressure), and therefore the experiments are usually done ex vivo. Kauer et al. [1] combined the video and pressure capturing components into a single device to simplify the measurement process, so that it can be performed in vivo during a surgical intervention. However, the device still needs to be in direct contact with the tissue, and only a small portion of the tissue can be measured due to the size of the device.

Elasticity reconstruction, or elastography, is a noninvasive method for acquiring strain or stiffness images using known external forces and a known displacement field [3], [4]. The reconstruction is usually formulated as an inverse problem of a physically-based simulation of elastic bodies, and a popular choice of the simulator is based on a linear elasticity model solved with the finite element method (FEM) [5], where the domain of the image is subdivided into tetrahedrons or hexahedrons called elements, with vertices known as nodes. Boundary conditions (displacement vectors or forces) on some of the nodes must be given to drive the simulation. Under this framework, nodal displacement vectors need to be computed based on a pair of images, and the force exertion mechanism needs to be controlled so that external forces can be measured. Otherwise, without measured forces, only relative elasticity values can be recovered. Ultrasound elastography [6], for example, compares two ultrasound images, one taken at the rest pose, and the other taken when a known force is applied. The displacement vector for each pixel can be estimated using cross-correlation analysis [3], [7] or dynamic programming [8] to maximize the similarity of echo amplitude and displacement continuity. Alternatively, in dynamic elastography (for example, magnetic resonance elastography (MRE) and vibroelastography), an MRI or ultrasound machine in tune with an applied mechanical vibration (shear wave) is used to find the displacement field [4], [9]. With known external forces and displacement field, the elasticity can be computed by solving a least-squares problem [10], [11], [12], if the algebraic equations resulting from the physical model is linear. A real-time performance has been reported using this direct method with a simplified 2D domain that assumes homogeneous material within a region [12]. Another type of method uses iterative optimization to minimize the error in the displacement field generated by the simulator [13], [14], [15]. Although slower than directly solving the inverse problem, this type of method does not assume linearity of the underlying physical model. A different kind of elastography [16], [17], [18] maximizes image similarity without requiring the displacement field or boundary conditions to be known, but the method relies on salient features within the object (such as the breast), which may not be present in CT images of organs such as the prostate. A phantom study applied the method to the prostate [17], but the model and boundary conditions are greatly simplified, and their method has not been applied to real patient data. A Bayesian framework has also been proposed to solve the elastography problem without requiring known boundary conditions [19]. That method, however, depends on assumptions about probability distribution functions and extensive sampling in a very high dimensional parameter space (elasticity and boundary conditions), which significantly limits the number of boundary nodes. While these methods are instrumental in their respective fields of interest, they are less well suited for a more general, multi-organ case where the image intensity may be almost constant within an organ, such as the prostate, and the lack of image details within the object makes it impossible to rely on pixel-wise correspondence. Moreover, the force exertion or vibration actuation mechanism can become complicated when the target tissues are deep inside the body. For example, for an elastography of the prostate, an actuator or a pressure sensor is sometimes inserted into the urethra or the rectum [20], [9], [21].

Elasticity parameters are also essential in cardiac function estimation, where sequential data assimilation [22], [23] has been applied to estimate simulation parameters and displacements simultaneously for dynamic mechanical systems. The parameters and observations of displacements (states) at each time step are modeled with a probability distribution, and a filtering procedure is applied over some time to estimate the states. Due to the computational complexity of the method, the number of estimated parameters has been very limited in work on cardiac function estimation [22]. On the other hand, our parameter space includes external forces as well as the Young's modulus, and the displacement field cannot be acquired directly from some common imaging modality like CT.

Accordingly, there exists a need for the ability to estimate biological tissue elasticity parameters where either the force or displacement is unknown or cannot be determined. Specifically, there exists a need for non-invasive estimation of biological tissue elasticity parameters and use of same for non-invasive cancer detection and cancer staging.

SUMMARY

We propose a general method for estimating elasticity and boundary forces automatically using an iterative optimization framework, given the desired (target) output surface. During the optimization, the input model is deformed by the simulator, and an objective function based on the distance between the deformed surface and the target surface is minimized numerically. The optimization framework does not depend on a particular simulation method and is therefore suitable for different physical models. We show a positive correlation between clinical prostate cancer stage (a clinical measure of severity) and the recovered elasticity of the organ. Since the surface correspondence is established, our method also provides a non-rigid image registration, where the quality of the deformation fields is guaranteed, as they are computed using a physics-based simulation.

According to one aspect of the subject matter described herein, a method for simulation-based estimation of elasticity parameters includes constructing a 3D model of an object comprising biological tissue, the model having a first shape and an elasticity value. A simulation iteration is then performed, which includes simulating the application of an external force to the model, causing the model to have a second shape, measuring the difference between the second shape and a target shape, and determining whether the measured difference between the second shape and the target shape is within a threshold of error. If the measured difference is not within the threshold of error, the process performs additional iterations using adjusted elasticity or force values until the measured difference is within the threshold of error, at which time the final elasticity and force values are reported. In one embodiment, the elasticity value is mapped to a diagnostic parameter, such as an indication of the possibility, presence, or stage of cancer.

According to another aspect of the subject matter described herein, a system for three dimensional estimation of elasticity parameters includes a simulator configured to simulate the application of an external force to a 3D model of an object comprising biological tissue, the model having a first shape and an elasticity value, the simulated external force having a force value and the application of the simulated force causing the model to deform to a second shape. The system also includes a parameter estimation module configured to measure a difference between the second shape and a target shape, to determine whether the measured difference between the second shape and the target shape is within a threshold of error, in response to a determination that the measured difference is not within the threshold of error, to adjust at least one of the elasticity value and the force value and repeated the simulating, measuring, and determining until the measured difference is within the threshold of error, and, in response to a determination that the measured difference is within the threshold of error, to map the elasticity value to a diagnostic parameter.

The subject matter described herein can be implemented in hardware or hardware in combination with software and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings, wherein like reference numerals represent like parts, of which:

FIG. 14 illustrates a pair of plots of percentage of variance explained versus the number of principal components for the finite element model of the bladder and the rectum shown in FIG. 4.

DETAILED DESCRIPTION

Figure 1:
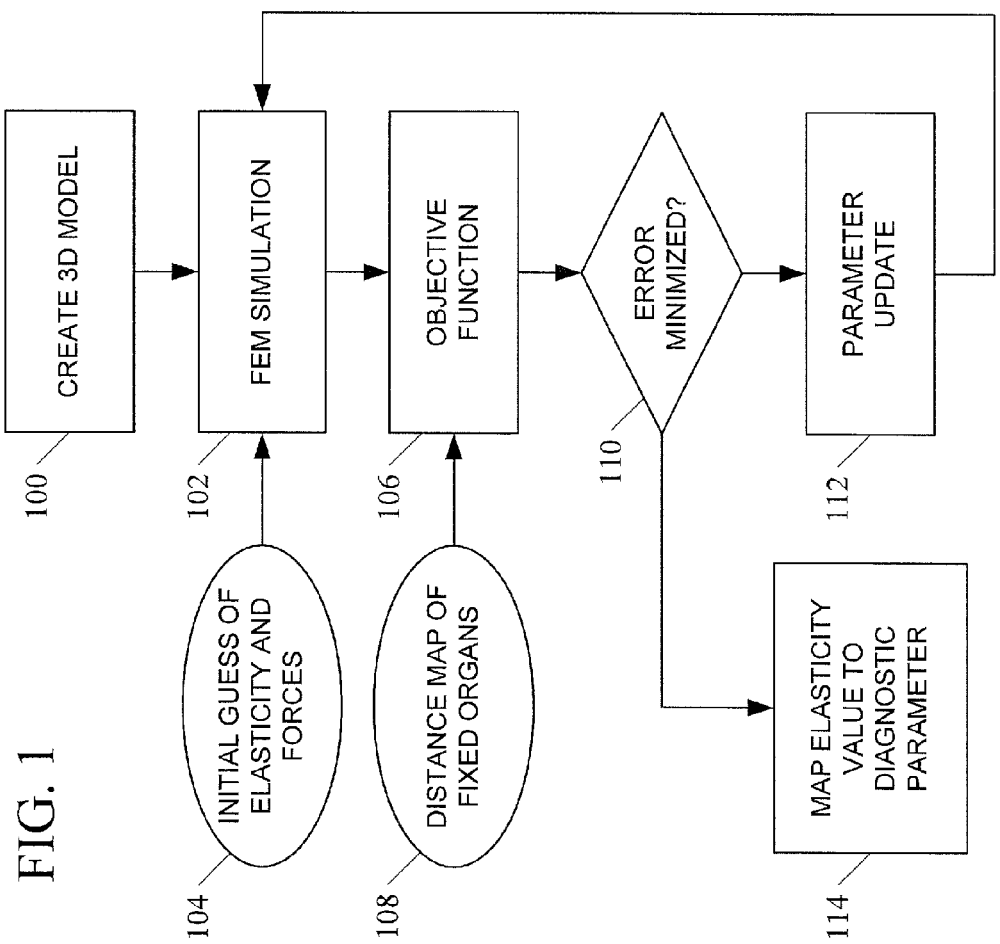
FIG. 1 is a flow chart illustrating an exemplary process for simulation-based estimation of elasticity parameters according to an embodiment of the subject matter described herein.

In accordance with the subject matter disclosed herein, systems, methods, and computer readable media for simulation-based estimation of elasticity parameters and use of same for non-invasive cancer detection and cancer staging are provided. Reference will now be made in detail to exemplary embodiments of the present invention, examples of which are illustrated in the accompanying drawings. Wherever possible, the same reference numbers will be used throughout the drawings to refer to the same or like parts.

I. INTRODUCTION

We propose an entirely passive analysis of a pair of images that only uses information about the boundaries of corresponding internal objects. We assume the images have already been segmented, that is, the organ boundaries have been found. Since we do not assume a good correspondence for pixels inside an object, the resolution of the resulting elastogram is limited to the object boundaries. Namely, we assume that the elasticity is fixed within each object whose boundary can be identified. Natural movements inside the body provide the deformation of the organs, and we do not need an additional force exertion or vibration actuating mechanism. We minimize the distance between the deformed reference surface and the target surface and optimize for the elasticities and boundary forces. Currently, as a simplification, we consider only Young's modulus (which measures the stiffness or elasticity of the material). It is the simplest parameter to work with, and it is also important in noninvasive cancer detection techniques. The general optimization framework extends naturally to the inclusion of other parameters such as Poisson's ratio (which measures compressibility of the material), and in fact is suitable for a variety of physical models. In our experiments, the images are obtained from a prostate radiotherapy, where there is one reference (planning) CT image and multiple target (daily) images for each patient, and the Young's moduli of the prostate recovered from the pairs of images are averaged. Our initial investigation involving 10 patient data sets shows that the recovered elasticity values positively correlate with the clinical tumor stages, which demonstrates its potential as a means of cancer stage assessment. Furthermore, compared broadly to other work on simulation parameter estimation, our method does not require the inclusion of forces as part of the input and can therefore avoid the process of measuring the external forces (at the cost of only providing relative force information in our results).

Our method also produces an image registration [24], [25] (pixel-wise correspondence between images) since the distance between the pair of surfaces (segmentations) is minimized. The FEM has been applied to image registration, given that the images are segmented [26], [27], [28], [29], [30], [31], [32]. Material properties, however, are not trivial to find from the images, and most authors use ex vivo experimental results to set up the materials. Moreover, due to the patient-to-patient differences, these material properties sometimes need hand adjustments. Alterovitz et al. [33] incorporated an optimization of Young's modulus and Poisson's ratio into an FEM-based registration, but the method has only been implemented for coarse 2D meshes. As a non-rigid image registration method, ours improves over previous simulation-based methods by providing an automatic means of finding the parameters that are missing in the images. Our current implementation uses both standard linear and nonlinear material models, but the optimization framework should be applicable to tissues with more advanced and complex physical models.

FIG. 1 is a flow chart illustrating an exemplary process for simulation-based estimation of elasticity parameters according to an embodiment of the subject matter described herein. In the embodiment illustrated in FIG. 1, at step 100, a 3D finite element model is constructed for the FEM simulation. In one embodiment, this model may be constructed based on a 3D image taken of the patient. At step 102, a FEM simulation is performed, using the 3D model created in step 100 and optionally also using an initial guess of elasticity of the model and forces being applied to the model, shown as input 104. The output of FEM simulation 102 is a deformed 3D model, referred to as the "moving" image. The simulation results use an objective function 106 to compare the output of the simulation to another 3D image taken of the patient, referred to as the "fixed" image, and usually showing a different deformation of the organs or structures being analyzed. Objective function 106 may take in as an input a distance map of fixed organs 108. The output of objective function 106 is the difference between the moving image and the fixed image, referred to as the "error". If the elasticity and forces used during FEM simulation 102 are exactly correct, the moving image will look exactly like the fixed image, i.e., the error will be zero. If not, there will be differences between the moving image and the fixed image, i.e., the error will be non-zero.

At step 110, the process checks to see if the error is minimized, i.e., below some acceptable threshold value. If not, then at step 112 one or more parameters into the FEM simulation (e.g., elasticity, forces, etc.) are updated and the process returns to step 102. Steps 102, 106, 110, and 112 are repeated until, at step 110, the error has been minimized to an acceptably low level, at which point the process moves to step 114. At step 114, the elasticity value last used by FEM simulation 102 is mapped to a diagnostic parameter, such as an indication of probability that the tissue being modeled is cancerous, pre-cancerous, or non-cancerous. Example calculations used during the process described in FIG. 1 will be discussed in more detail, below.

Figure 2:
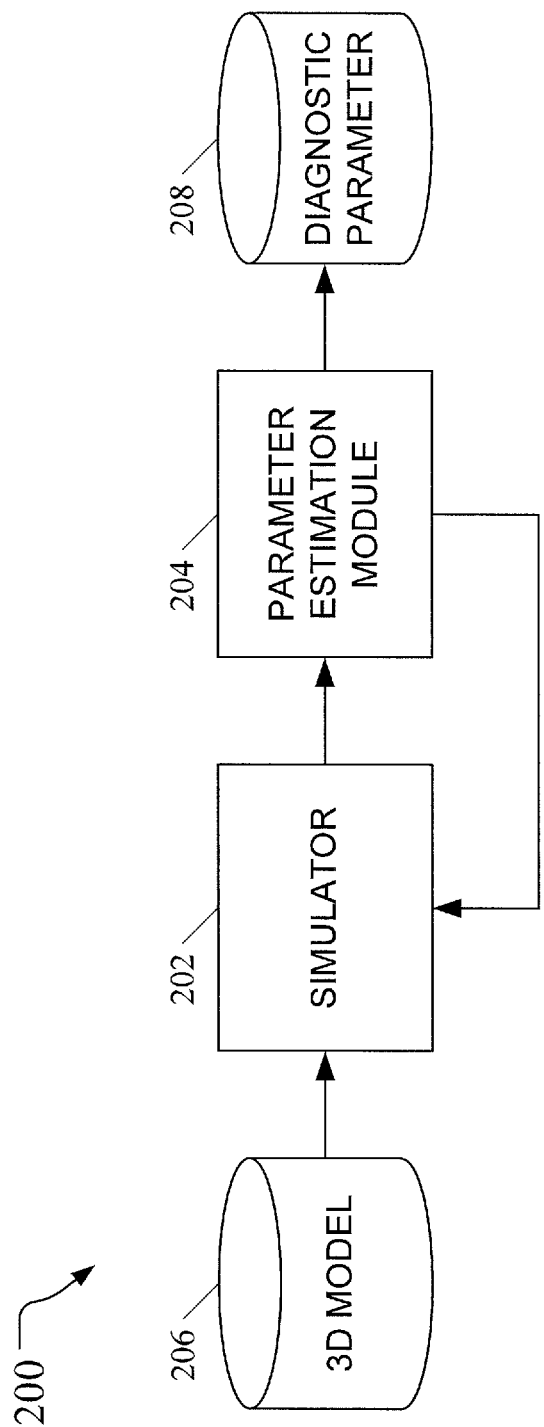
FIG. 2 is a block diagram illustrating an exemplary system for three dimensional estimation of elasticity parameters according to an embodiment of the subject matter described herein.

FIG. 2 is a block diagram illustrating an exemplary system for three dimensional estimation of elasticity parameters according to an embodiment of the subject matter described herein. In the embodiment illustrated in FIG. 2, system 200 includes a simulator 202 configured to simulate the application of an external force to a 3D model of an object comprising biological tissue, the model having a first shape and an elasticity value, the simulated external force having a force value and the application of the simulated force causing the model to deform to a second shape. System 200 also includes a parameter estimation module 204 configured to measure a difference between the second shape and a target shape, to determine whether the measured difference between the second shape and the target shape is within a threshold of error, in response to a determination that the measured difference is not within the threshold of error, to adjust at least one of the elasticity value and the force value and repeated the simulating, measuring, and determining until the measured difference is within the threshold of error, and, in response to a determination that the measured difference is within the threshold of error, to map the elasticity value to a diagnostic parameter. In the embodiment illustrated in FIG. 2, system 200 may include a database 206 for storing the 3D model(s) used by simulator 202. In the embodiment illustrated in FIG. 2, either simulator 202 or parameter estimation module 204 may store the diagnostic parameter so determined in a database 208 for that purpose. In one embodiment, database 208 may be used to store tables or other information used to map the elasticity value to the diagnostic parameter.

Figure 3:
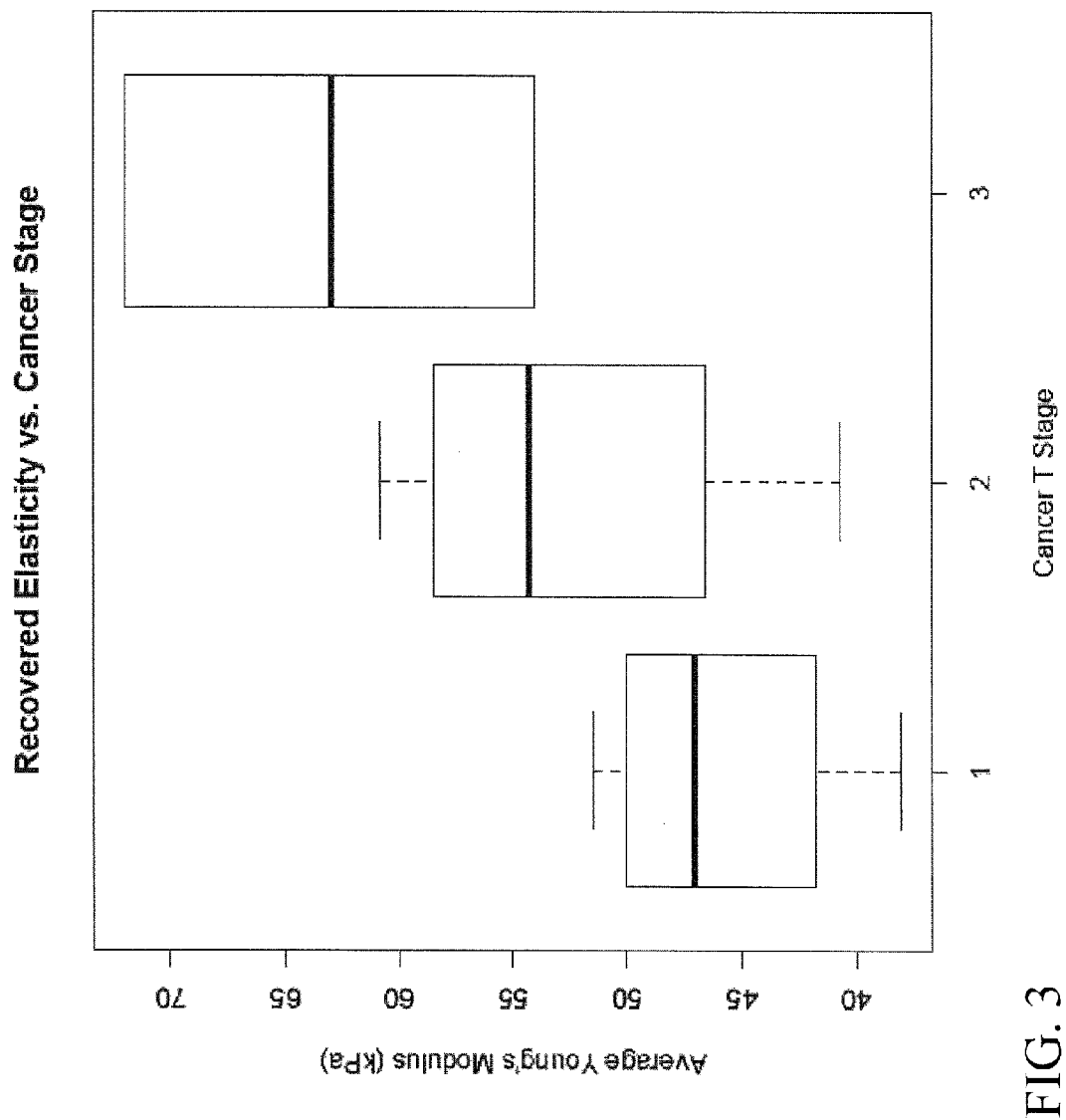
FIG. 3 is a graph showing an example correlation between elasticity determined by exemplary methods and systems for simulation-based estimation of elasticity parameters according to embodiments of the subject matter described herein to cancer T stage measured in prostate cancer patients.

FIG. 3 is a graph showing an example correlation between elasticity determined by the methods and systems above to cancer T stage measured in prostate cancer patients. In the example shown in FIG. 3, the average elasticity of tissue, measured in Young's modulus (kPa) is in the range of 37-52 for stage 1, between 40 and 62 for state 2, and between 55 and 73 for stage 3. Thus, if the result of a simulation performed by system 200 indicates an elasticity of 57, it can be inferred using FIG. 3, that the tissue is cancerous, i.e., somewhere between stage 2 and stage 3, but closer to stage 2. Likewise, if the simulation results show an elasticity less than 37, this may indicate tissue that is pre-cancerous but perhaps heading towards stage 1.

The specific algorithms used by exemplary methods and systems of the subject matter described herein will now be described in detail. We explain the elastic model and the optimization scheme in Section II, followed in Section III by experimental results using two synthetic scenes and 10 sets of real CT images to demonstrate the feasibility of our method. We conclude with a summary.

II. METHOD

The idea of the algorithm is to optimize a function based on the separation between corresponding organ boundaries. In each iteration, the objective function is computed by first simulating and deforming the surface using the current set of parameters, and then computing surface distances. We consider only the elasticity value (Young's modulus), with Poisson's ratios being chosen according to previous work on simulation-based medical image registration [30].

The inputs to the correspondence problem are two segmented images: a fixed image with segmentation $S_f$ and a moving image with segmentation $S_m$. The bones are already aligned using a rigid registration method described in [34]. Each segmentation is represented as a set of closed triangulated surfaces, one for each segmented object. We construct a tetrahedralization of the moving volume such that each face of $S_m$ is a face in the tetrahedralization, so that $S_m$ is characterized entirely by its set of nodes. Our optimization framework is built on a physically-based simulator that generates deformation fields with n unknown parameters $x=[x_1, \ldots, x_n]^T$, and a numerical optimizer to minimize an objective function $\Phi(x):\mathbb{R}^n \rightarrow \mathbb{R}$ defined by the deformation and surface matching metrics. During the optimization process, the physical model is refined in terms of more accurate parameters and converges to a model describing the deformation needed for the particular surface matching problem. Here we use the linear FEM to illustrate the optimization scheme, although the framework can also be incorporated with a nonlinear FEM. A flow chart of our algorithm is shown in FIG. 1 and will be explained in detail in this section.

A. Linear Elasticity Model and Finite Element Modeling

In the optimization loop, the displacement field $u=[u,v,w]^T$ is always generated by a physically-based simulation, where the FEM is used to solve the constitutive equations of the linear elasticity model. Assuming isotropic linear elasticity, we can write $\sigma=D\epsilon$, where $\sigma$ is the stress vector induced by the surface forces, $\epsilon$ is the strain vector defined by the spatial derivatives of the displacement u, and D is a matrix defined by the material properties (assuming an isotropic material, the properties are Young's modulus E and Poisson's ratio v).

Assuming linear elasticity, the stress vector $\sigma=[\sigma_x,\sigma_y,\sigma_z,\tau_{xy},\tau_{yz},\tau_{xz}]^T$ is a linear transformation of the strain vector $\epsilon$ (change of shape or size), and the transformation is defined by the material properties (assuming isotropic material, the properties are Young's modulus and Poisson's ratio) of the elastic body. The strain vector is defined by the derivatives of the deformation $u=[u,v,w]^T$:

$$\epsilon = \left[\frac{\partial u}{\partial x}, \frac{\partial v}{\partial y}, \frac{\partial w}{\partial z}, \frac{\partial u}{\partial y}+\frac{\partial v}{\partial x}, \frac{\partial v}{\partial z}+\frac{\partial w}{\partial y}, \frac{\partial u}{\partial z}+\frac{\partial w}{\partial x}\right]^T = Lu$$

and the simulation essentially amounts to solving the constitutive equation for the deformation u, given the external forces $[f_x,f_y,f_z]^T$:

$$\frac{\partial \sigma_x}{\partial x} + \frac{\partial \mathcal{T}_{xy}}{\partial y} + \frac{\partial \mathcal{T}_{xz}}{\partial z} + f_x = 0$$
$$\frac{\partial \mathcal{T}_{xy}}{\partial x} + \frac{\partial \sigma_y}{\partial y} + \frac{\partial \mathcal{T}_{yz}}{\partial z} + f_y = 0$$
$$\frac{\partial \mathcal{T}_{xz}}{\partial x} + \frac{\partial \mathcal{T}_{yz}}{\partial y} + \frac{\partial \sigma_z}{\partial z} + f_z = 0$$

To solve the equations numerically, we approximate the derivatives of the deformation with the FEM, where the domain is subdivided into a finite set of elements, and each element consists of several nodes.

Figure 4:
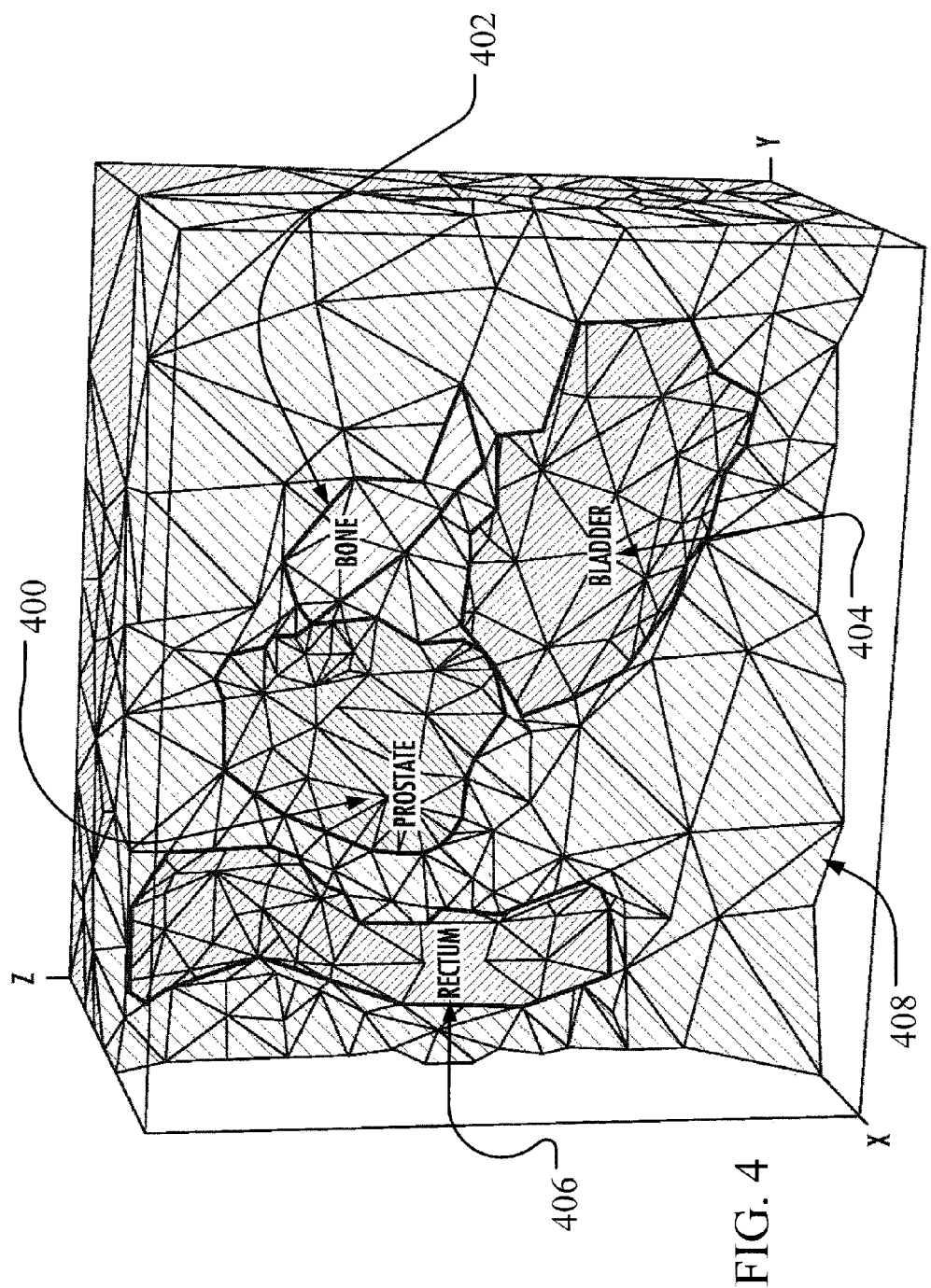
FIG. 4 illustrates an exemplary finite element model used in the methods and systems disclosed herein, the model using four-node tetrahedral elements.

FIG. 4 shows the finite element model used in one of our experiments, where four-node tetrahedral elements are used. The model is of a 3D domain that includes a prostate 400, bone 402, a bladder 404, a rectum 406, and surrounding tissues 408. The deformation field $u^{el}$ for any point p within an element is approximated with a piecewise linear function $$\hat{u}^{el}(p)=\Sigma_{j=1}^{ne}u_j^{el}N_j^{el}(p)$$

where $u_j^{el}$ is the deformation of the j-th node of the element, and $N_j^{el}(p)$ is the linear shape function that has value one at node j and is zero at all other nodes and outside of the element. After combining the approximated piecewise linear equation for each element, the resulting linear system is $$Ku=F \qquad (1)$$

where K is called the stiffness matrix, which depends on the material properties (Young's modulus and Poisson's ratio) and the geometry of the elements; F is a vector of external forces. For a 3D domain with $N_n$ nodes, K is a $3N_n \times 3N_n$ matrix. Notice that since both K and F are unknown, they can be scaled by the same factor without changing the output deformation field. Therefore, unless we know the exact values of the forces, only the relative values of the material properties can be recovered.

To make the nodes deform, some boundary conditions need to be enforced, either by assigning displacement values or by assigning forces to some nodes. If all the surface nodes, including boundaries between two materials, are assigned displacement values, then the simulation is essentially an interpolation of the displacement field from surface matching results. This means that the elasticity values only affect internal nodes, for which we do not know the target positions. Therefore the elasticity cannot be recovered. Instead, we only assign boundary conditions to a part of the surface nodes, and other surface nodes without boundary conditions will be affected by the relative elasticities. For example, in a simulation of the male pelvis area, the bladder and the rectum are usually the organs that drive the deformation of the prostate, while the pelvic bone is considered static. An intuitive choice is to apply boundary conditions on boundary nodes of the bladder, the rectum, and the pelvic bone, and set all other entries in the force vector to zero (no external forces), as proposed in [30].

B. Sensitivity Study

Since our method is based on the assumption that the deformed surface depends on both the elasticity and the external forces, we first conduct an experiment of forward simulations using different parameter values to see how sensitive the surface is to these parameters.

Figure 5:
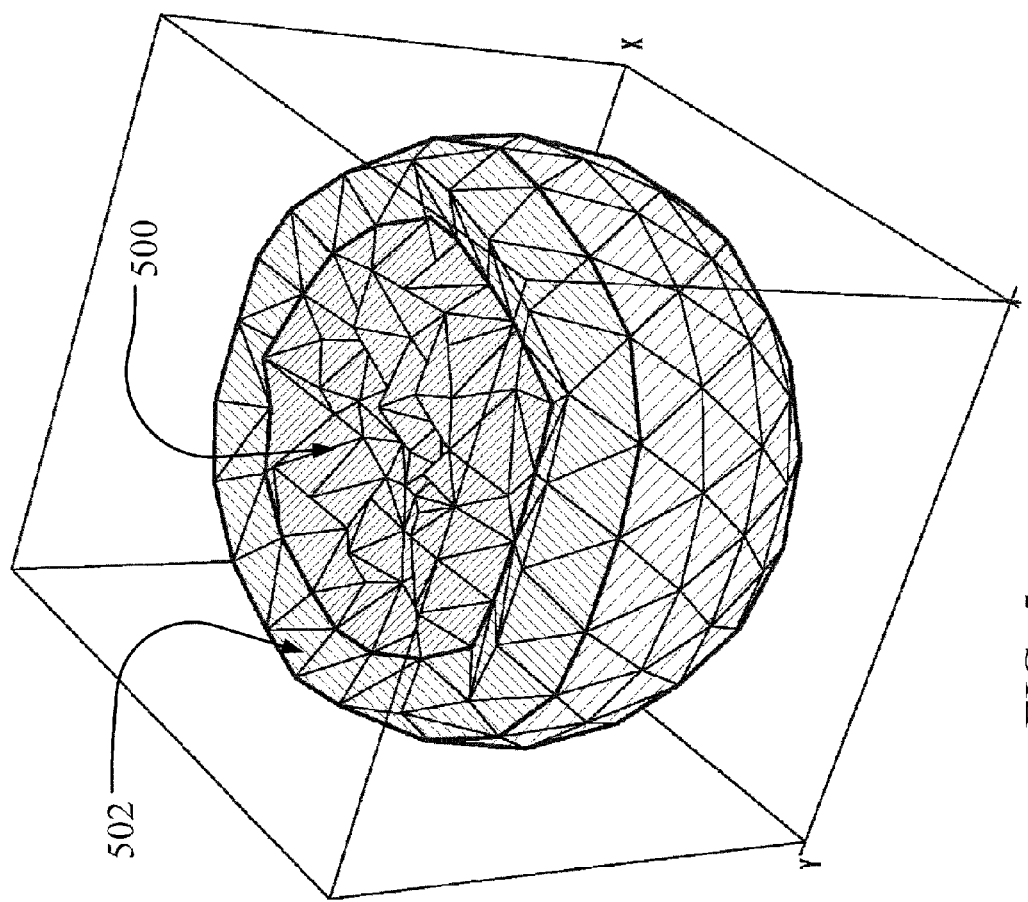
FIG. 5 illustrates an exemplary finite element model of a synthetic scene used to determine the sensitivity of modeled surfaces to simulated parameters of elasticity and external forces.
Figure 6A:
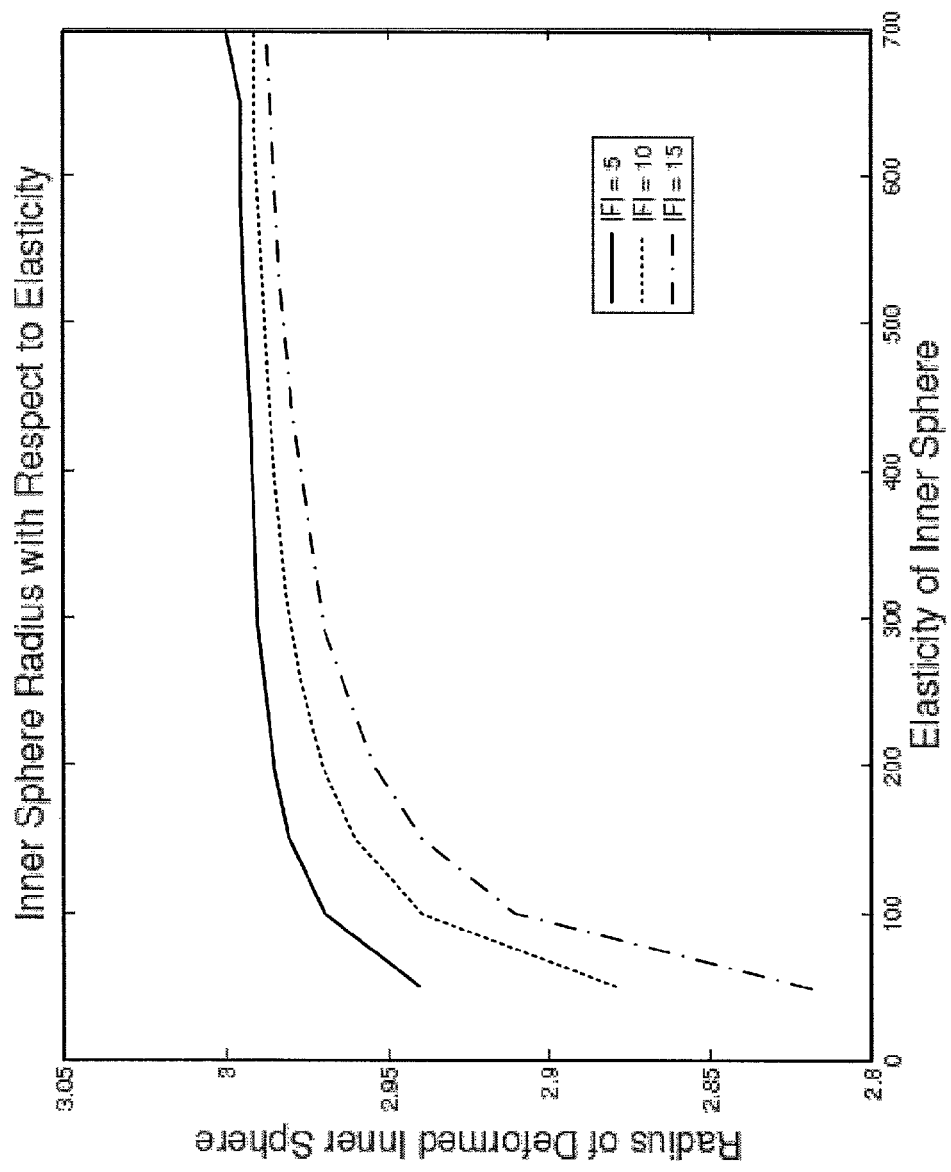
FIGS. 6A through 6F are graphs showing plots of sphere radius versus elasticity value/force magnitudes for the synthetic scene shown in FIG. 5.
Figure 6B:
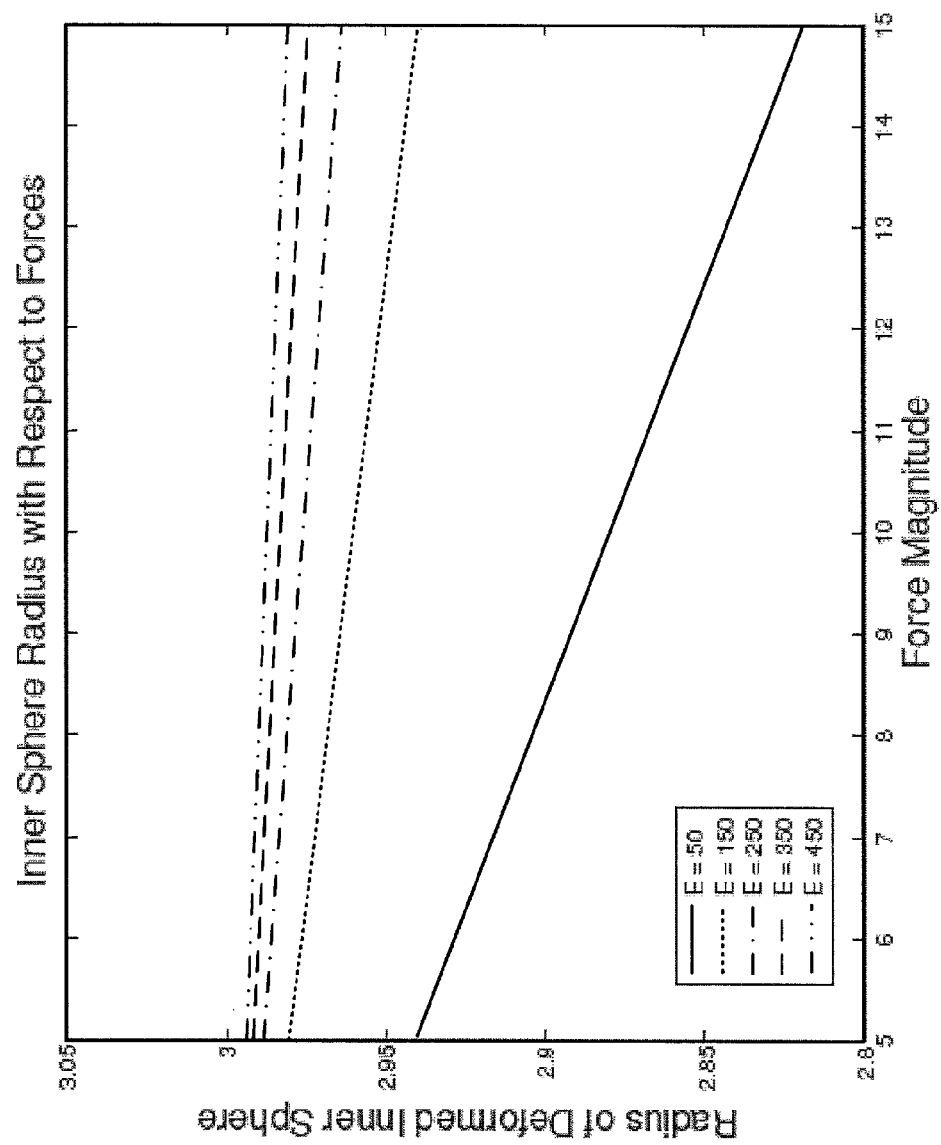
Figure 6C:
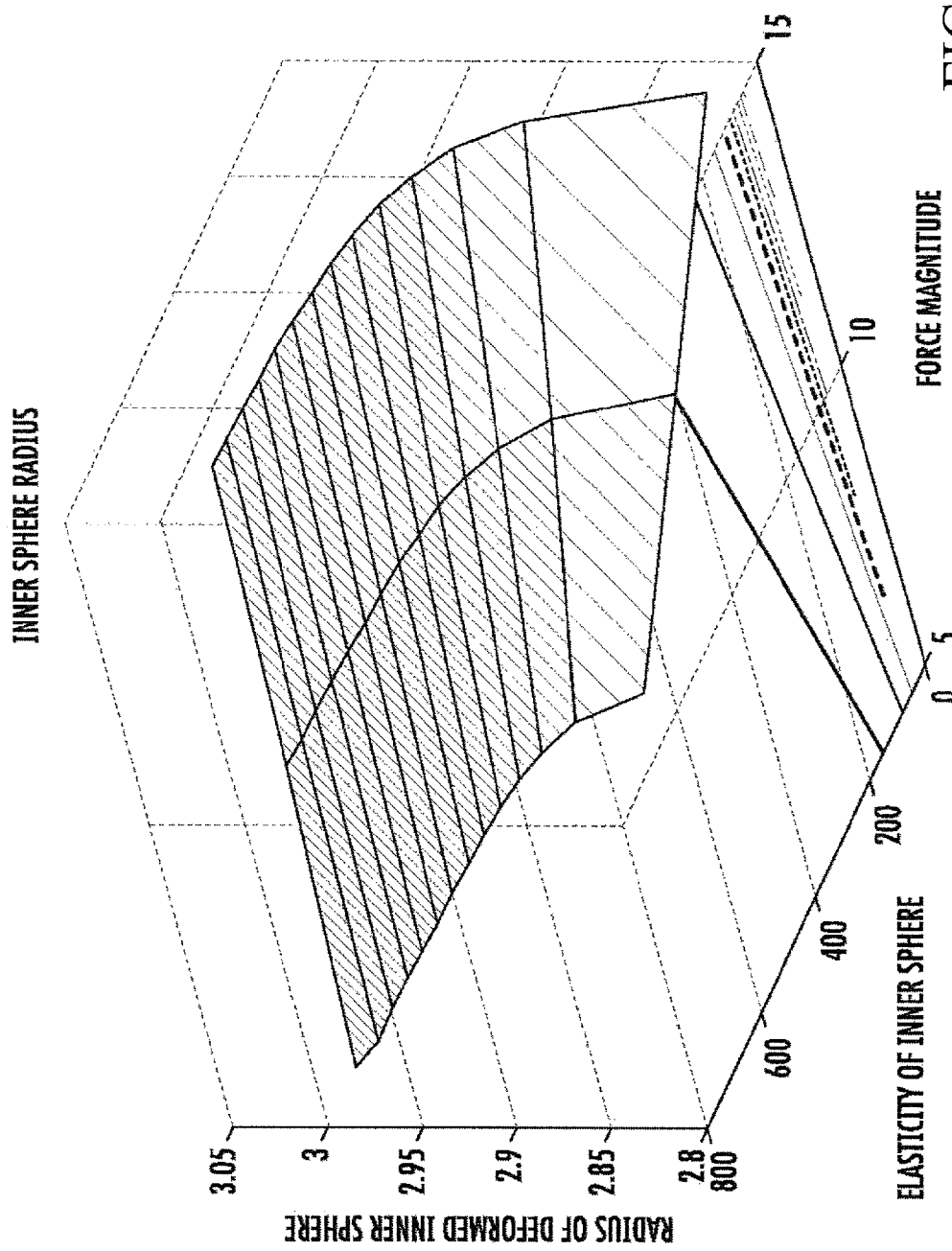
Figure 6D:
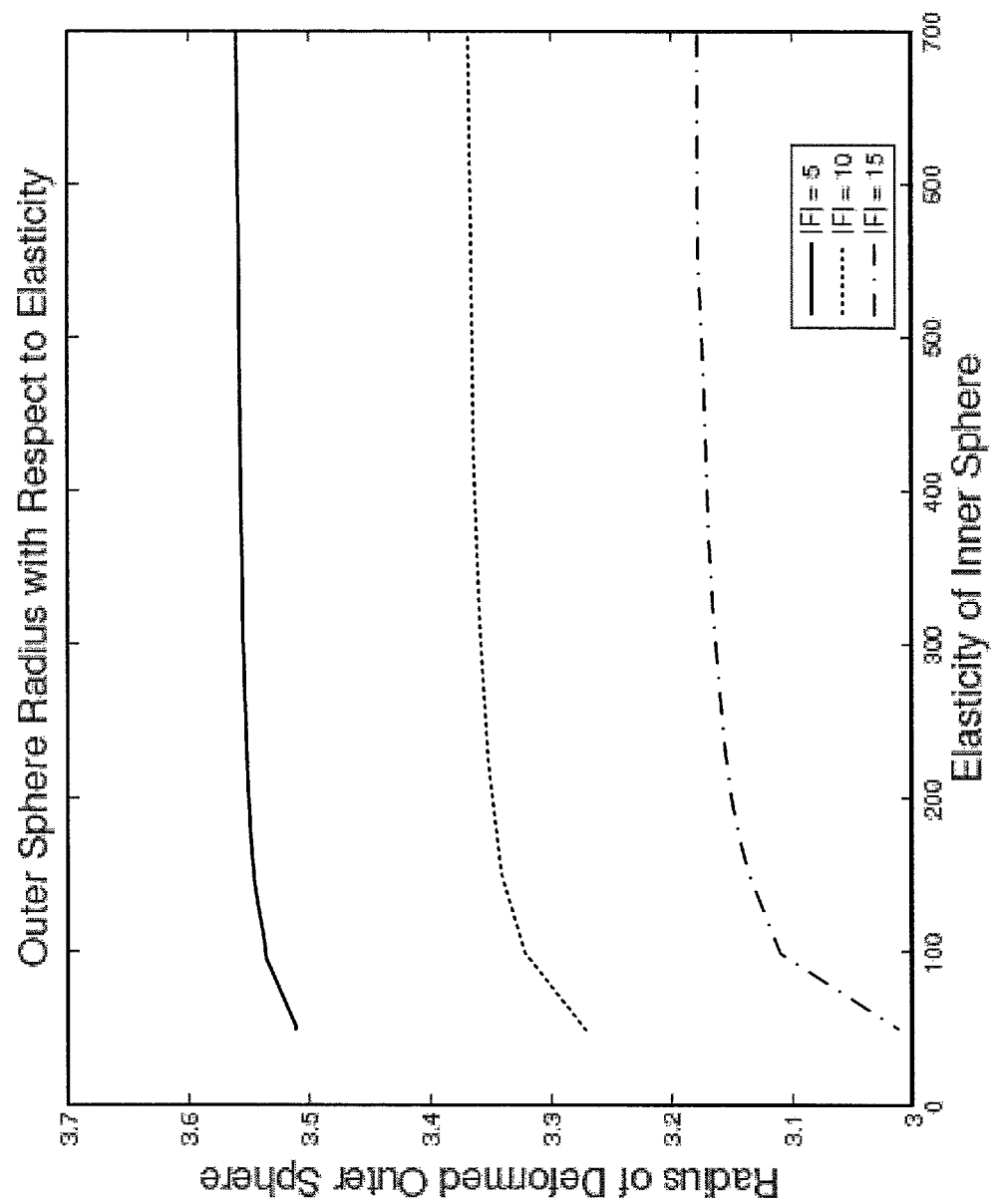
Figure 6E:
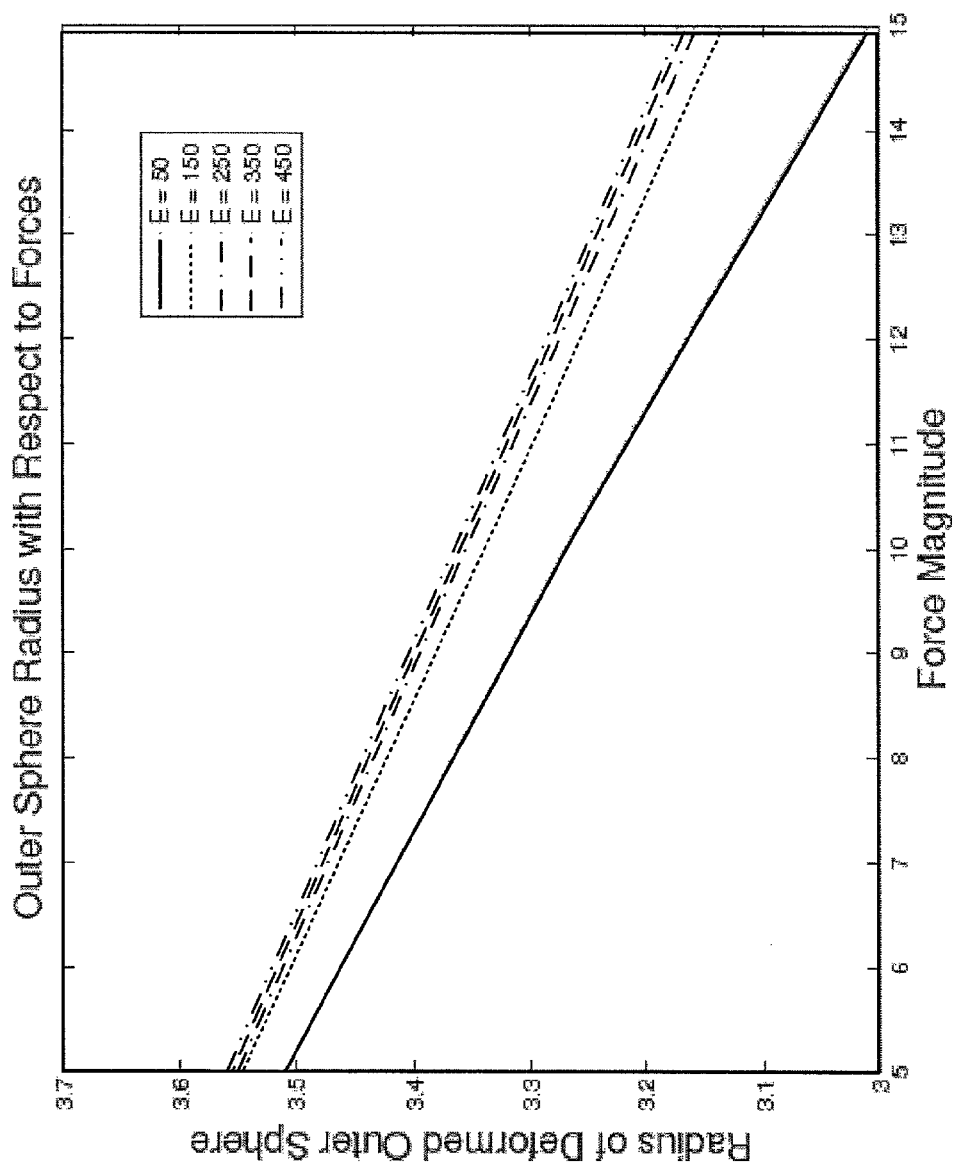
Figure 6F:
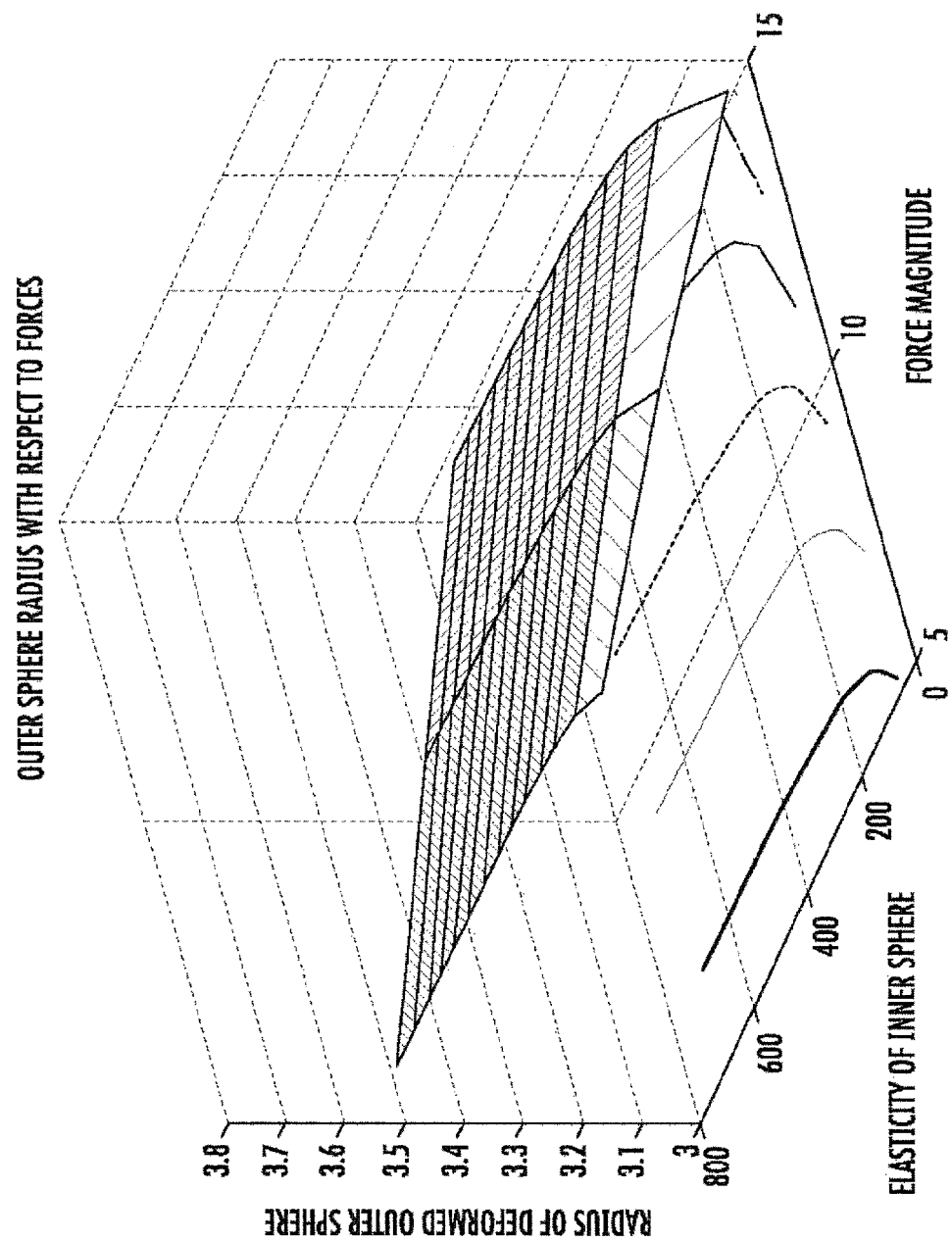

FIG. 5 shows a synthetic scene that consists of two concentric spheres that form two regions, one inside the inner sphere 500, and the other between the two spheres 502. We fix the elasticity of the outer region and alter the elasticity of the inner sphere, as only the ratio of the two elasticity values matters. A force with a specified magnitude pointing towards the center of the spheres is applied on each node of the outer surface, and no external forces are applied on the inner surface. Several simulations using different elasticities of the inner region and force magnitudes were performed.

FIGS. 6A through 6F show plots of the sphere radius versus the elasticity value and versus force magnitude. Notice that in these plots, the slope is much higher when the elasticity is low for each curve, which indicates that the shapes of both spheres are much more sensitive to the elasticity when the elasticity value is lower. These results suggest that our ability to recover the parameters is limited by how stiff the object is. When an object has a very high stiffness, its shape becomes insensitive to the parameters. In this case, the shape can still be recovered, but the resulting parameters may not be accurate. Notice that the problem of solving for elasticity and for boundary forces is ill-posed with a single object. For example, drawing horizontal lines at some inner radius value in the plots in FIGS. 6A-F would give multiple combinations of elasticity and external forces. However, when both the inner and outer surfaces are taken into account, the problem becomes well-posed: in the two-dimensional space formed by elasticity value and force magnitude, there is one curve that implies some radius of the inner sphere (an isocontour on the xy-plane in FIG. 6C) and another curve that results in some radius of the outer sphere (an isocontour on the xy-plane in FIG. 6F). The solution is at one of the intersections of the two curves, and we can eliminate unwanted solutions by limiting the range of elasticity and force magnitude according to experimental results on the specific materials.

C. Distance-Based Objective Function

The parameters needed in the simulator are x=[E; F], where E consists of the material properties (in our case, the Young's moduli), and F is the vector of external forces on boundary nodes. The objective function to be minimized is defined as the difference between the segmentations in the moving and target images, $$\Phi(x) = \frac{1}{2} \Sigma_{v_l \in S_m} \| d(v_l + u_l(x), S_f) \|^2 \quad (2)$$

Here u(x) is the deformation field computed by the simulator with parameters x, interpreted as a displacement vector for each surface node $v_l$ in the tetrahedralization. The notation d(v,S) denotes the shortest distance vector from the surface S to the node v, and the sum is taken over all nodes of the moving surface.

The gradient of the objective function, which is needed in the iterative optimization, is given by the chain rule, $$\nabla \Phi(x) = \sum_{v_l \in S_m} \left[\frac{\partial u_l}{\partial x}\right]\left[\frac{\partial d(v_l + u_l, S_f)}{\partial u_l}\right] d(v_l + u_l(x), S_f) \quad (3)$$

$$= \Sigma_{v_l \in S_m} J_u^T J_d^T d(v_l + u_l(x), S_f)$$

where $$J_u = \left[\frac{\partial u_i}{\partial x_j}\right]$$

is the Jacobian matrix of u(x) with respect to the parameters, and $$J_d = \left[\frac{\partial d_i}{\partial u_j}\right]$$

is the Jacobian matrix of d with respect to the deformation vector. Here we use the bracket [•] to represent a matrix and the curly braces {•} to denote a vector. Each column of $J_d$, namely $$\left\{\frac{\partial d(v_l + u_l, S_f)}{\partial u_j}\right\}$$

is the derivative of $d(v_l+u_l,S_f)$ with respect to the j-th spatial coordinate (j=1,2,3). The derivatives of u with respect to the material properties are computed by differentiating both sides of Equation (1), $$\left[\frac{\partial K}{\partial E_j}\right] u + K \left\{\frac{\partial u}{\partial E_j}\right\} = 0 \quad (4)$$

Therefore we have $$\left\{\frac{\partial u}{\partial E_j}\right\} = -K^{-1}\left[\frac{\partial K}{\partial E_j}\right] u.$$

The Jacobian matrix can then be computed by solving for each column of $J_u$. The derivatives with respect to the boundary forces are computed in the same manner; by taking derivatives of both sides of (1), we have $$\left[\frac{\partial K}{\partial F_j}\right] u + K \left\{\frac{\partial u}{\partial F_j}\right\} = e_j,$$

where $e_j$ is the j-th coordinate vector. On the right hand side, only the j-th entry is nonzero since $$\frac{dF_i}{dF_j} = 0$$

when $i \neq j$. And since K is independent of $$F_j, \frac{\partial K}{\partial F_j} = 0.$$

Therefore we can solve for each column of the Jacobian with the equation $$K\left\{\frac{\partial u}{\partial F_j}\right\} = e_j.$$

In practice, $d(v_I + u_I(x), S_f)$ can be looked up in the precomputed vector distance map of the fixed organ, $S_f$, and the derivatives $\partial d/\partial u_j$ can be approximated with a centered finite difference operator applied on the map.

Figure 7:
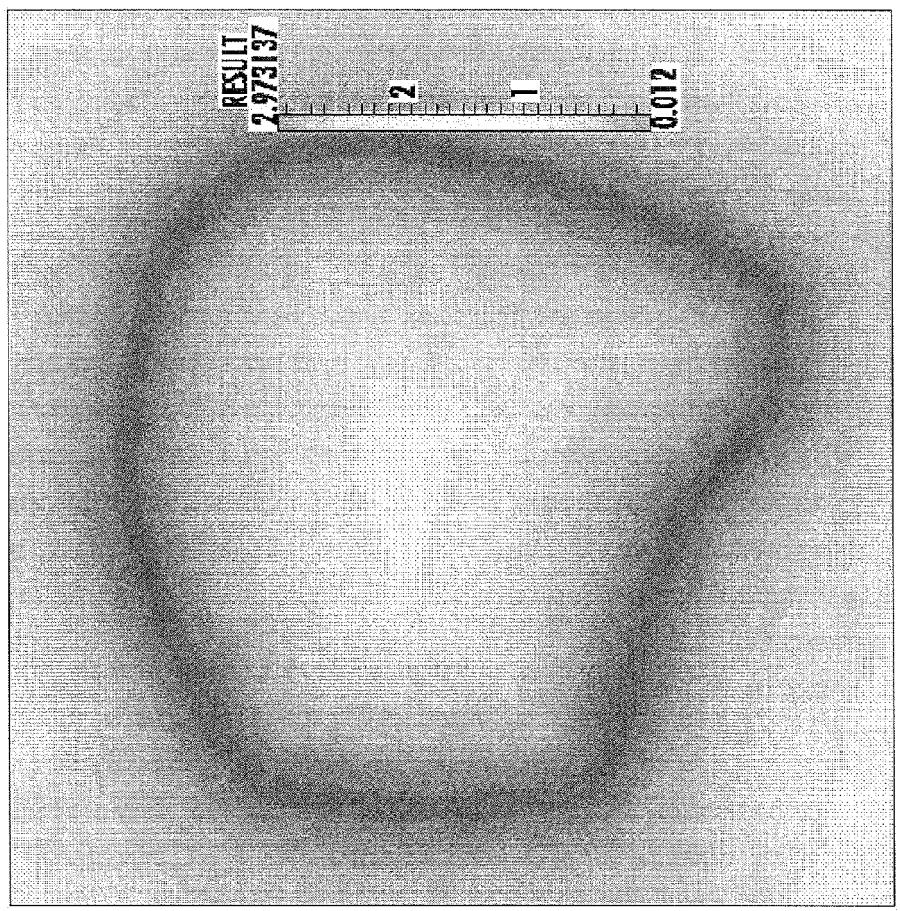
FIG. 7 illustrates an exemplary distance map used in a simulation of the finite element model shown in FIG. 4.

FIG. 7 shows one of the distance maps used in our experiments. Notice that the physical model can be different, as long as the derivatives $\partial u_i/\partial x_j$ can be computed. In experiments, however, we observed that the magnitudes of gradients with respect to the material properties, $\|\partial\Phi/\partial E\|$, are about 1000 times smaller than that with respect to the forces, $\|\partial\Phi/\partial F\|$, which caused the material properties to converge very slowly. To obtain a faster convergence of E, we embed the optimization of the forces into the objective function evaluation at each E value. That is, every time $\Phi(E)$ is evaluated, a full optimization of F is performed with the fixed value of E.

D. Numerical Optimization

We use a line search scheme for optimization: in each iteration k, we find a descent direction $p_k$ find an optimal step size a in that direction with a line search algorithm, and then update the parameters with $x_{k+1} = x_k + \alpha p_k$. The descent direction can be computed by using Newton's method to solve the equation $\nabla\Phi = 0: p_k = -B_k^{-1} \nabla\Phi(x_k)$, where B is the Hessian matrix $$\left[\frac{\partial^2 \Phi}{\partial x_i \partial x_j}\right].$$

A modified Newton's method has been used in elasticity reconstruction [14], but the Hessian matrices can only be approximated and are usually ill-conditioned. Alternatively, we can use a Quasi-Newton method (4) such as the BFGS formula to avoid computing the Hessian [35].

Quasi-Newton methods can reduce the computation yet still retain a super-linear convergence rate. A line search enforcing the curvature condition $(s_k^T y_k > 0)$ needs to be performed to keep the approximate Hessian positive definite. In our case, the number of parameters can be in the thousands, and therefore we adopt a limited-memory quasi-Newton method known as the L-BFGS method [35].

E. Initial Guess of Parameters

A good initial guess can prevent the optimizer from getting stuck in a local minimum. Our initial guess for the forces is based on the distance field of the target surface: each node requiring a boundary condition is moved according to the distance field to compute a Dirichlet boundary condition. A forward simulation is performed using the set of boundary conditions and the initial guess of elasticities, and the output deformation is used, via (1), to compute the corresponding forces, which become the initial guess for the forces.

In the case of medical image registration, the initial guess of the elasticity is chosen based on knowledge of the simulated organs. Our example images involve two materials: the prostate and the surrounding tissue. There have been ex vivo experiments on the prostate using different elasticity models. Krouskop et al. [36] reported an elastic modulus of 40-80 kPa for normal prostate tissue, 28-52 kPa for BPH tissue, and 80-260 kPa for cancerous tissue when receiving 4% compression.

They also reported 10-30 kPa for breast fat tissue. Based on these numbers for fat tissue, we chose an elasticity value of 10 kPa for the tissue surrounding the prostate. This value is fixed, in our calculations, since only the ratio of the elasticity values matters.

The initial guess of elasticity for the prostate is chosen by a parameter search: we perform force optimizations with several elasticity values between 30 kPa and 200 kPa and choose the elasticity with the lowest objective function value after the force optimization.

Figure 8:
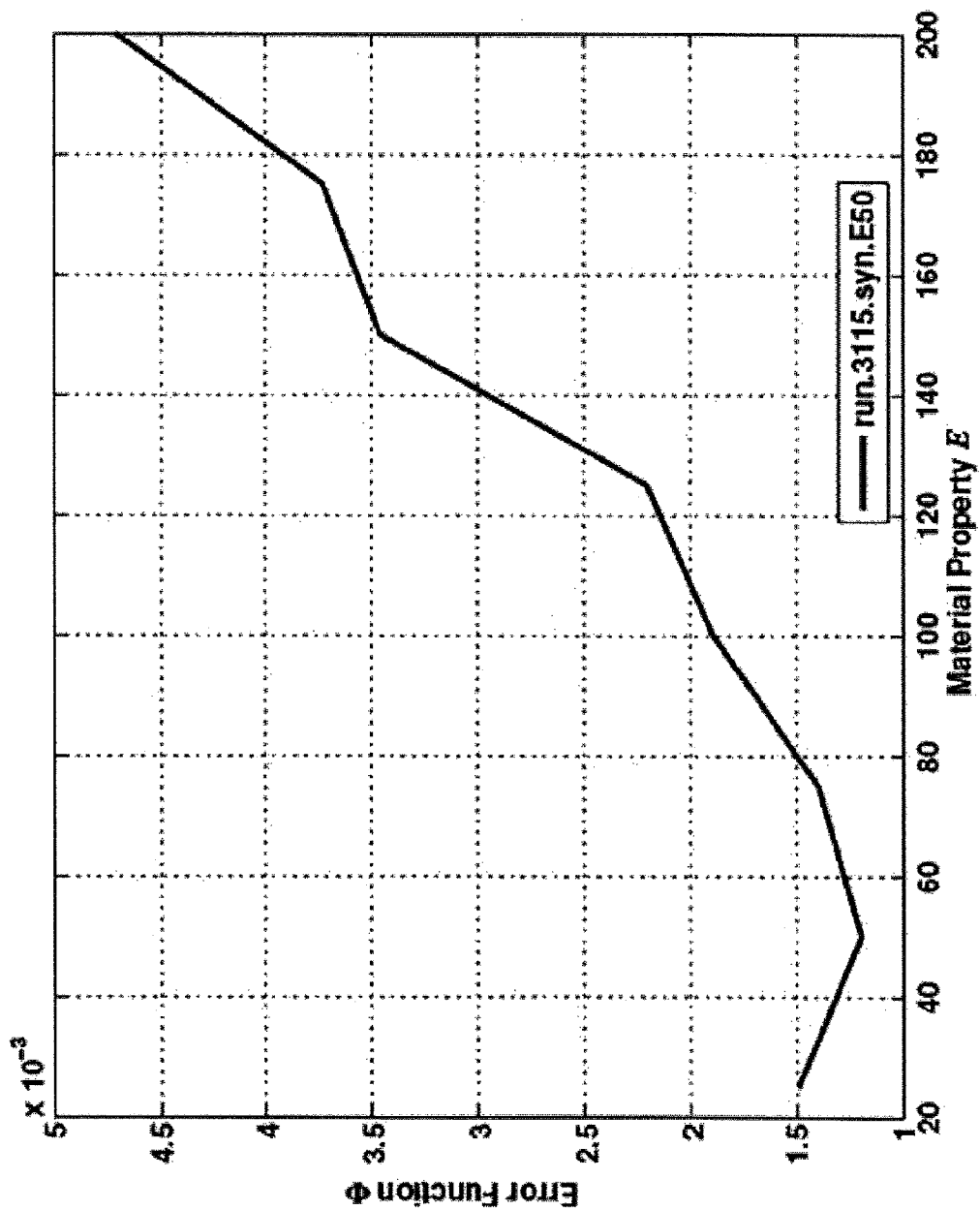
FIG. 8 is a plot illustrating the result of an exemplary parameter search, showing the output of the error function versus a material property.

FIG. 8 shows a plot of an example result of the parameter search, where the target surfaces are generated by artificially deforming a set of organ boundaries, so that the true elasticity value is known. The plot shows that the parameter search successfully located the global minimum in the synthetic case with multiple organs. In our experiments using synthetic and real organ boundaries of the male pelvis area, we have observed similar curves with a single minimum. If more than one local minimum is observed, an optimization can be performed using each of these values as the initial guess. To reduce the computation time, we use a lower-resolution mesh for the parameter search, and the resulting optimal forces are used as the initial guess when using a higher-resolution mesh for elasticity optimization.

III. EXPERIMENTS

We used the male pelvis area as the test scene. To build the reference surfaces, we obtained segmentations of a 3D CT image of the male pelvis area, including the surfaces of the bladder, prostate, rectum, and bones. A tetrahedral finite element mesh is constructed from a set of reference surfaces, as shown in FIG. 4. The corresponding target surfaces are used to compute the distance map, as shown in FIG. 7. In the tetrahedral mesh, the bladder and the rectum are made hollow to reflect the actual structure, and the bones are fixed during the simulations. Since the prostate is the main organ of interest, we apply forces only on the boundaries of the bladder and the rectum to reduce the uncertainty on the prostate, which will be moved by surrounding tissues. The setting also reflects the fact that the bladder and the rectum are the organs that have larger deformations due to different amount of fluid and gas, and the prostate is usually deformed by their movement.

During the iterative optimization, the objective function is evaluated over the surfaces of the bladder, rectum, and prostate. The Poisson's ratios are fixed (0.40 for the prostate and 0.35 for surrounding tissues, chosen based on literature in image registration [28], [37], [30]), and we optimize for the elasticity values because of its importance in noninvasive cancer detection. Since only the relative values of material properties can be recovered, we fix the Young's modulus of the surrounding tissues (the region outside all organs and bones) to 10 kPa and optimize that of the prostate.

We tested our algorithm on two types of surface data. First, we tested the accuracy of the optimization scheme using synthetic target surfaces generated by forward simulations, so that we know the true elasticity values. We then applied the technique to prostate cancer stage assessment based on multiple segmented target images of the same patient to show applicability to real data. Since the distances between reference and target surfaces are minimized, we also compare the visual result (the warped image) with that of an image-based image registration method.

The reference and target organ surfaces are obtained from real 3D CT images of the male pelvis area using the software MxAnatomy (Morphormics, Durham, N.C.), and the bones are segmented using ITK-SNAP [38]. Given the moving surfaces in the form of triangle meshes, the tetrahedral model for the entire domain is built with the software TetGen [39], and the library ITK [40] is used to compute the vector distance maps of the target surface. The FEM simulator uses the linear algebra library PETSc [41].

Mesh Generation:

The image segmentation was done with an early semi-automatic version of software MxAnatomy. For the prostate, the user typically needed to specify 15-20 initial boundary points on five image slices, and it usually took 20 minutes to segment the three main organs (prostate, bladder, and rectum) in a CT image. The semi-automatic segmentation of bones (ITK-SNAP) requires some initial pixels (specified with a few spheres) that are roughly in line with the bones, and the algorithm iteratively grows or shrinks from these initial pixels until an optimal binary image of the bone is achieved. It usually takes 15 minutes for the segmentation of bones. Once the surface meshes are generated, the tetrahedralization takes a few seconds using the software TetGen.

A. Synthetic Scene with Multiple Organs

To test how well our algorithm recovers elasticity values, we use synthetic target surfaces generated with known elasticity and boundary conditions. The target surfaces are generated by a forward simulation with Dirichlet boundary conditions acquired from a real pair of segmented images applied to the bladder and rectum surfaces.

Figure 9:
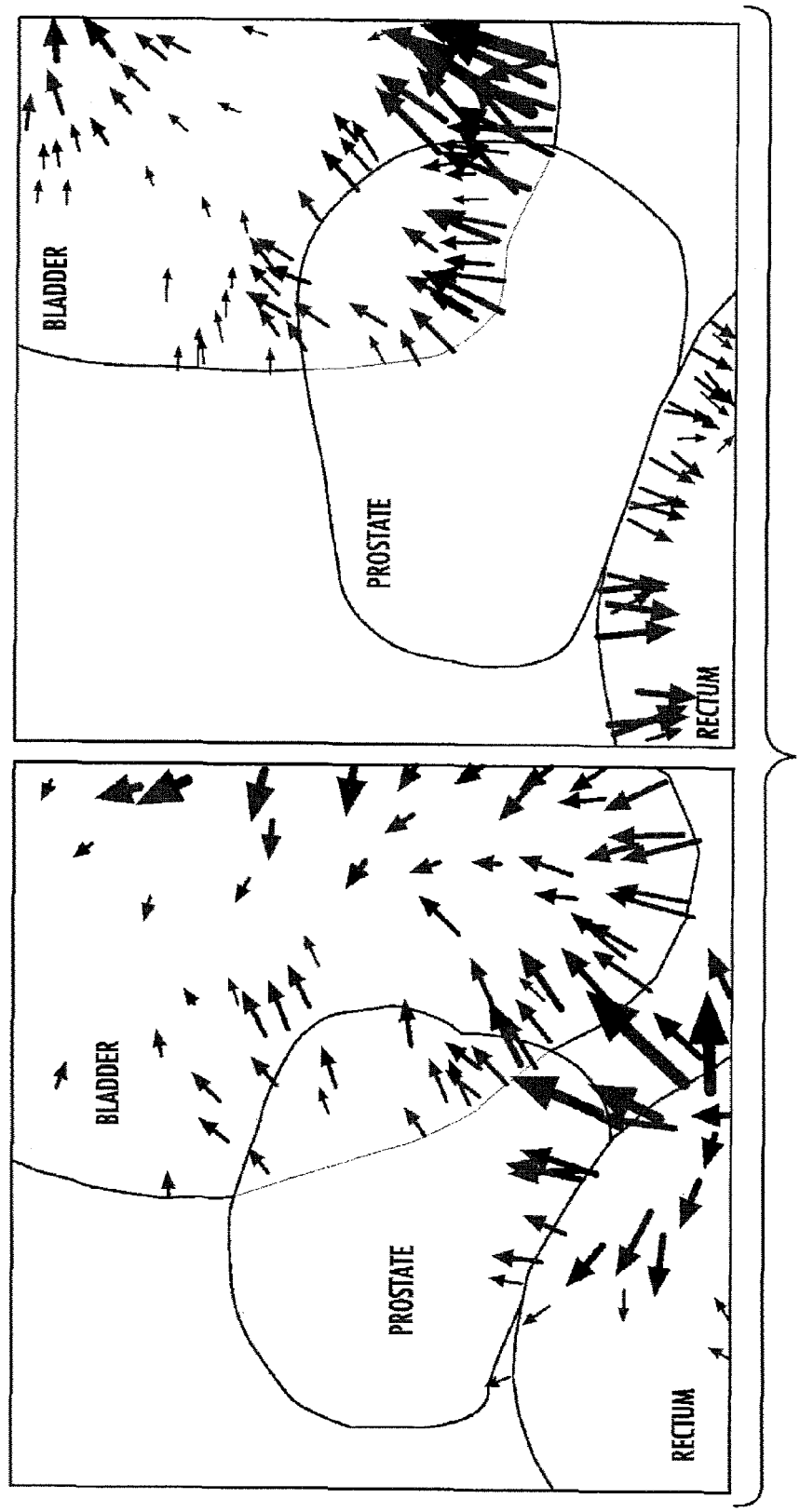
FIG. 9 are two synthetic scenes showing moving surfaces and boundary conditions as scaled arrows.

FIG. 9 shows the moving surfaces and boundary conditions in the two synthetic scenes, where the boundary conditions are shown with scaled 3D arrows. The elasticity value of the prostate is controlled, and we can therefore compare the value recovered by our method to the ground truth. We tested our algorithm with three elasticity values, and the results are shown in Table I.

B. Non-Invasive Assessment of Prostate Cancer Stage

To show the effectiveness of our method applied to prostate cancer assessment, we repeated the experiments on the multi-organ settings, but with both the deformed and target surfaces taken from segmented 3D CT images of the male pelvis area. We consider 10 patient data sets taken throughout courses of radiotherapy for prostate cancer. Each patient data set consists of a set of reference surfaces (bladder, prostate, rectum, and bones), which is from the CT image (reference image) taken before the radiotherapy, and multiple sets of target surfaces, each of them representing the internal structures in one daily CT image during the therapy. The reference image is taken about a week before the first treatment, and treatment (target) images are typically taken twice a week. For each patient data set, we repeated the process of deforming the reference surfaces toward a set of target surfaces with our method, so that one elasticity value of the prostate is recovered for each daily image.

Figure 10A:
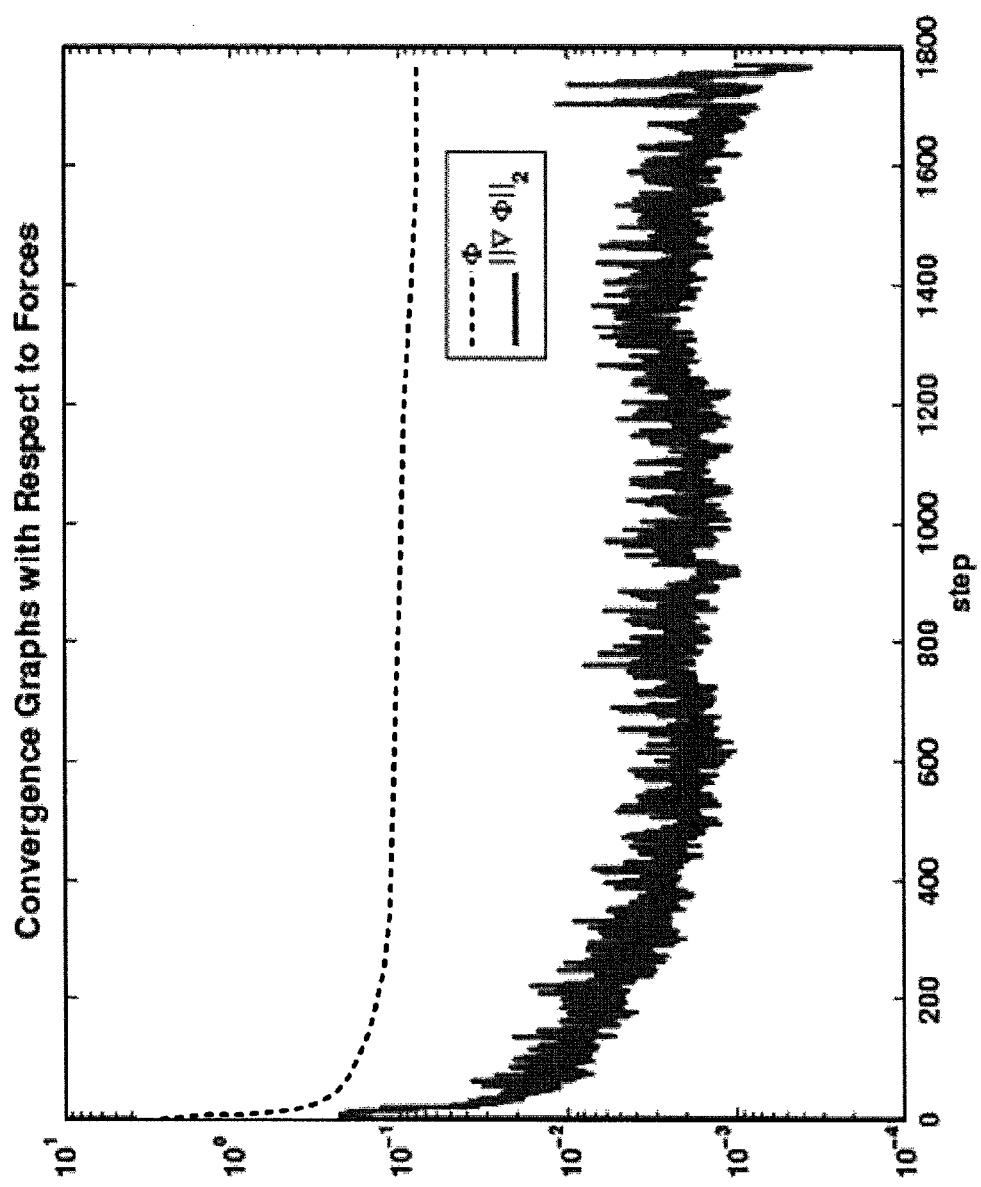
FIGS. 10A and 10B are convergence graphs with respect to forces and with respect to material properties, respectively, of the objective function and the gradient of the objective function versus simulation iterations.
Figure 10B:
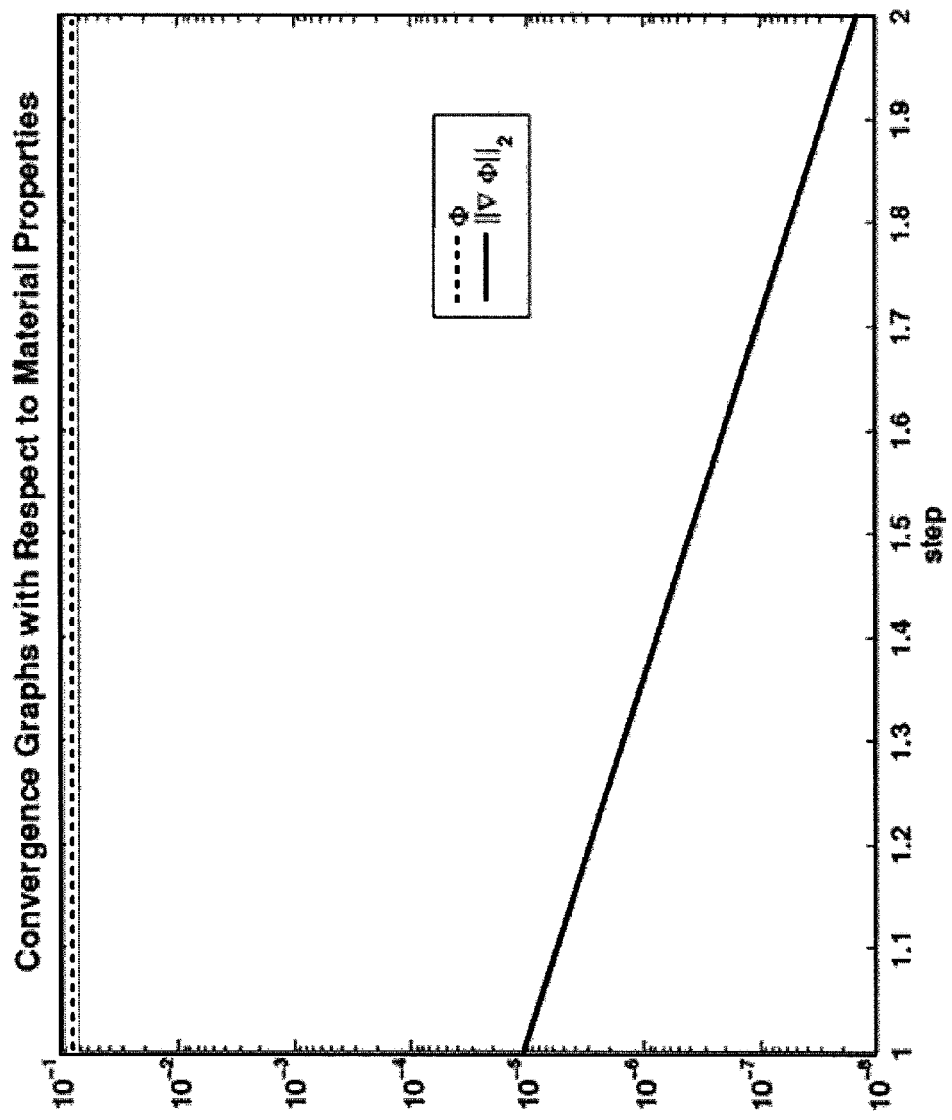

FIGS. 10A and 10B are convergence graphs (plots of $\Phi$ and $\|\nabla\Phi\|$ versus iteration number) and for boundary forces and for the material property, respectively, from a typical image pair. Note that the optimization of forces was done in batches (in each evaluation of $\Phi(E)$), and the convergence graph for force optimization is the result of concatenating the steps for optimizing F. With our current code, each iteration for the force optimizer takes about 19 seconds for a mesh with 34,705 tetrahedral elements and 6,119 nodes on a Xeon X3440 CPU, and the total number of iterations is around 1,700 (the total time is about nine hours), which means that our current implementation is only suitable for off-line processes. Note that we have not utilized any parallelism in the FEM computation. In the future, we plan to explore faster implementations of the FEM, such as those utilizing a many-core processor and reduced-dimension models.

Each of the 10 patient data sets tested include 6 to 17 sets of target surfaces (daily images), namely 112 target images in total, and the recovered elasticity values of the prostate for each patient are shown in Table II. Notice that the recovered values from all image pairs are within the range suggested in the literature [36], and the result shows consistency within each patient.

TABLE I

| True Elasticity (kPA) | | 50 | 100 | 150 | 200 | 250 | 300 | 350 |
|---|---|---|---|---|---|---|---|---|
| Scene 1 | Recovered Value | 39 | 101.18 | 158.79 | 141.57 | 136.65 | 204.45 | 176 |
| | Relative Error | −2% | +1.2% | +5.9% | −29.2% | −45.3% | −31.9% | −49.7% |
| Scene 2 | Recovered Value | 51.33 | 102.90 | 167.5 | 225.0 | 222.91 | 275.0 | 277.97 |
| | Relative Error | +2.7% | +2.9% | +11.7% | +12.5% | −10.8% | −8.3% | −20.6% |

The optimization process is terminated when $\|\partial\Phi/\partial E\|<10^{-7}\|E\|$ and $\|\partial\Phi/\partial F\|<10^{-4}\|F\|$ or when the optimizer cannot find a direction in the parameter space that reduces the value of the objective function. The relative error is less than 12% in the cases where the elasticity values do not exceed 150 kPa, which corresponds to an elasticity ratio of 15 between the prostate and the surrounding tissue. Notice that according to the literature [36], the ratio is already beyond the range for normal tissues and is within the range for cancerous tissues. Therefore we expect to see worse accuracy in the case of stiffer cancerous tissues.

TABLE II

| | Number of Targets | Average Young's Modulus (kPa) | Std. Deviation | Clinical T-Stage |
|---|---|---|---|---|
| Patient 1 | 8 | 48.60 | 2.41 | T1 |
| Patient 2 | 6 | 53.99 | 10.28 | T3 |
| Patient 3 | 7 | 71.97 | 4.35 | T3 |
| Patient 4 | 6 | 60.81 | 1.25 | T2 |

TABLE II-continued

| | Number of Targets | Average Young's Modulus (kPa) | Std. Deviation | Clinical T-Stage |
|---|---|---|---|---|
| Patient 5 | 16 | 38.06 | 13.91 | T1 |
| Patient 6 | 16 | 45.42 | 10.26 | T1 |
| Patient 7 | 17 | 40.67 | 16.34 | T2 |
| Patient 8 | 15 | 52.40 | 7.72 | T2 |
| Patient 9 | 9 | 51.47 | 7.50 | T1 |
| Patient 10 | 12 | 56.19 | 7.95 | T2 |

The aim of this study is to assess the relation between the recovered elasticity value and the cancer stage of each patient, under the assumption that prostates with more advanced tumors have higher stiffness. A common cancer staging system is the TNM (Tumor, lymph Nodes, Metastasis) system, where the clinical T-stage describes the size and extent of the primary tumor [42]. The definitions of T-stages are shown in Table III.

TABLE III

| Stage | Definition |
|---|---|
| TX | Primary tumor cannot be assessed |
| T0 | No evidence of primary tumor |
| T1 | Clinically inapparent tumor neither palpable nor visible by imaging |
| T2 | Tumor confined within prostate |
| T3 | Tumor extends through the prostate capsule |
| T4 | Tumor is fixed or invades structures other than seminal vesicles |

We focus on the T-stage because of its relevance to the stiffness of the prostate. The clinical T-stages for the patients are shown in the last column of Table II. In order to analyze the data statistically, we treat the average recovered elasticities and tumor stages as two random variables and use numbers 1, 2, and 3 to represent T-stages Ti, T2, and T3, respectively (TO and T4 are not present in our data sets), and we test if the recovered elasticity values and the T-stages are positively correlated. The resulting Pearson (linear) correlation coefficient is 0.662, and the p-value for the two-sided correlation test is 0.037, which indicates a significant positive correlation between the recovered elasticity values and the T-stages, based on a p-value threshold of 0.05. Since the tumor stage values are discrete and might be nonlinear with respect to the elasticity, a rank correlation coefficient, such as the Spearman's rank correlation $\rho$, may be more suited for the test. From the samples we have Spearman's $\rho=0.701$ and an estimated p-value of 0.024, which shows again a significant positive correlation. The box plot of the elasticity values and cancer stages is shown in FIG. 3.

C. Study: Inhomogeneous Materials

We assume a constant material property within an organ due to the limitation of the image modality, where the intensity is almost constant within the prostate, so that it is impossible to segment the tumor. The elasticity values recovered by our method are therefore "average" values in some sense, and a higher recovered elasticity indicates either a stiffer tumor or a larger tumor. Since the clinical T-stage for prostate cancer depends on the extent of the tumor, we conducted a study to show the correlation between the tumor size and the recovered elasticity value.

Figure 11:
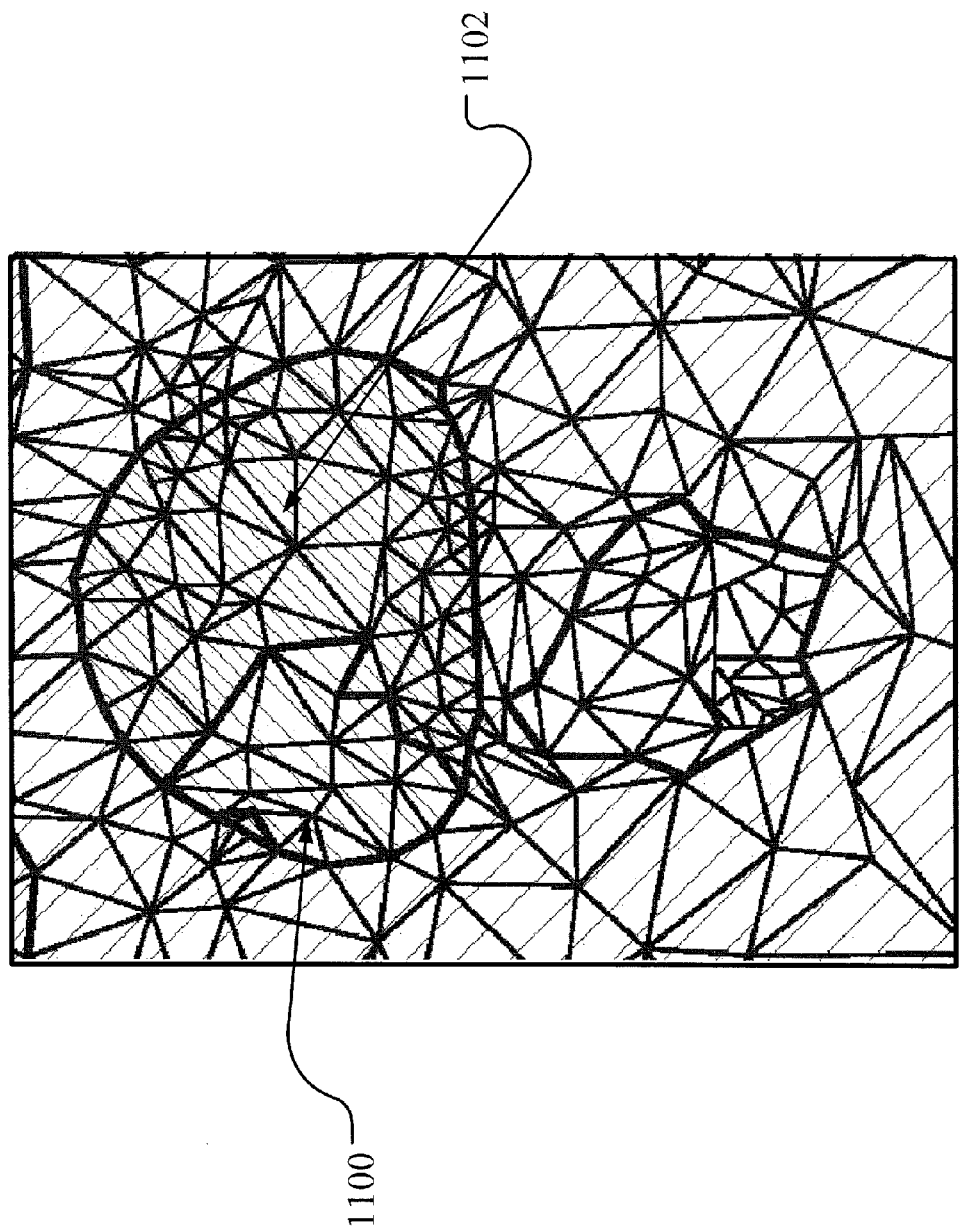
FIG. 11 illustrates an exemplary finite element model of a prostate gland that contains a tumor.

FIG. 11 shows a finite element model based on the settings in the synthetic multi-organ experiments in Section 111-A, in which was embedded an additional tumor 1100 inside the prostate 1102 for generating synthetic target surfaces. The elasticity values for the tumor and the normal prostate tissues are set to 100 and 50 kPa, respectively.

Notice that in the elasticity recovery process, we do not know the extent of the tumor due to the imaging limitation, and we only recover one value for the prostate. Table IV shows the recovered elasticity values with different tumor sizes relative to the entire prostate. The results show increasing elasticity values with increasing tumor sizes in both scenes. Even though we assume homogeneous materials, the recovered values can still be used as an indicator of the extent of the tumor and are therefore correlated to cancer stages.

TABLE IV

| | Tumor size/Prostate Size (%) | | | |
|---|---|---|---|---|
| | 10% | 25% | 50% | 75% |
| Scene 1 | 51.24 | 59.98 | 62.15 | 63.44 |
| Scene 2 | 53.55 | 56.90 | 69.92 | 70.00 |

D. Application: Registration of Segmented CT Images

Since the distance between the fixed and moving surfaces is minimized during the optimization process, we also have an image registration as a result of optimizing for forces and elasticities. In our experiments, the final average value of the objective function is 0.09, corresponding to an RMS error of 0.01 cm, and a maximum of 0.22 cm, which are within the image resolution, 0.1×0.1×0.3 cm.

Figure 12:
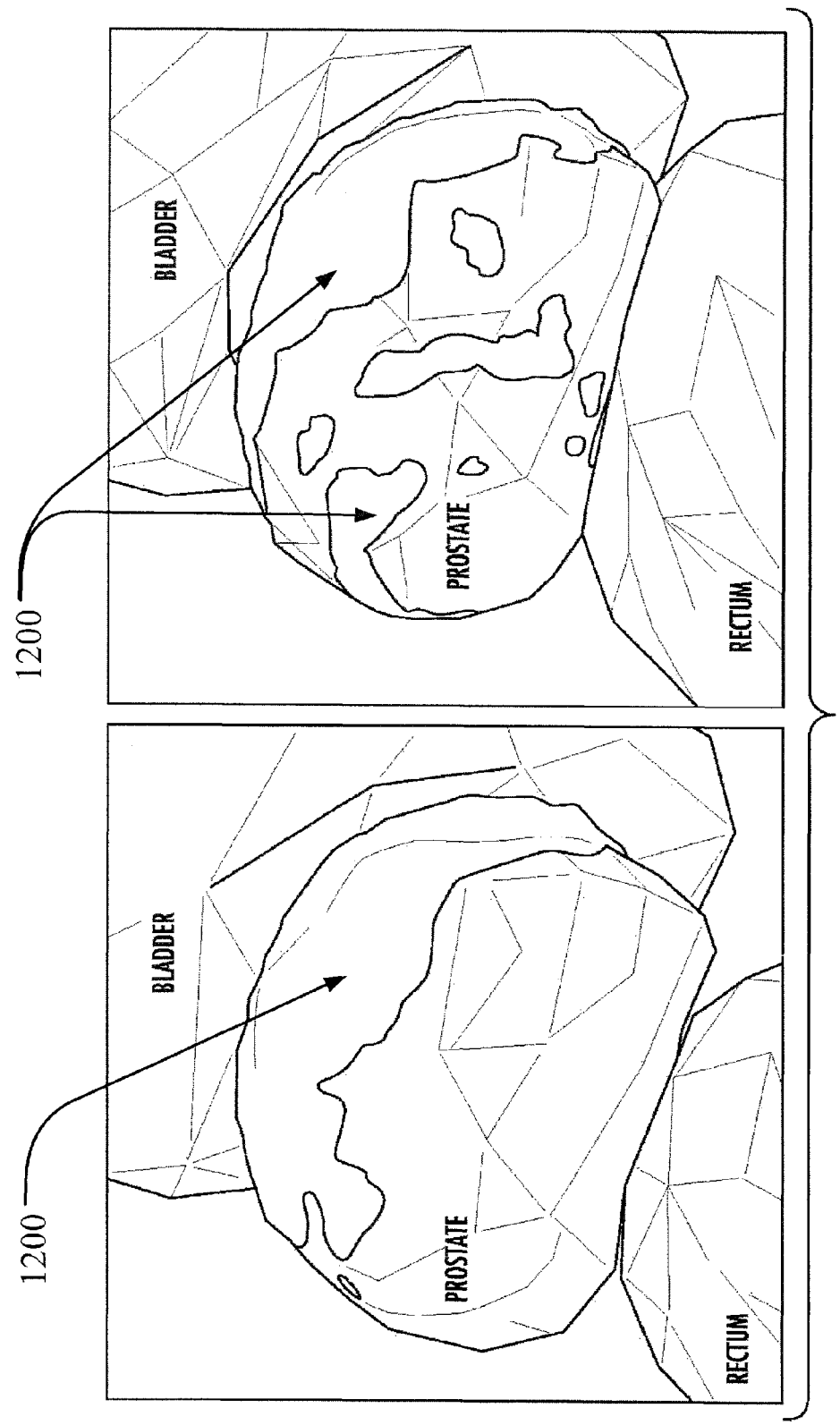
FIG. 12 illustrates a pair of images, each image showing the deforming surfaces of a bladder and rectum with external forces applied, with the simulated surface of the prostate shaded and the target surface of the prostate shown in white.

FIG. 12 shows a 3D close-up view of the deforming surfaces from an image pair, where the surfaces of the bladder and the rectum are those with external forces applied, and the target surface 1200 of the prostate is shown in white.

We also compared our registration results with a popular image-based approach, the Demons method [43], by looking at some landmarks inside the prostate. In most cases, the image intensity is almost constant inside an organ, but five of the patient data sets (a total of 32 image pairs) we experimented on have three "seeds" implanted in the prostate for location tracking during each treatment fraction, resulting in bright spots that can be observed in the CT image. The distance between the target and the deformed landmark positions from the two methods are shown in Table V, and the two-tail t-tests for paired samples (distances) show that our method produces statistically significantly better results in three out of five patient data sets (with a p-value threshold of 0.05).

TABLE V

| | | Demons | | Our Method | | Paired |
|---|---|---|---|---|---|---|
| | # Target Images | Avg. (cm) | Std. dev. | Avg. (cm) | Std. dev. | t-test p-value |
| Patient 1 | 8 | 0.27 | 0.17 | 0.26 | 0.18 | 0.07 |
| Patient 2 | 6 | 0.21 | 0.11 | 0.16 | 0.11 | 0.03 |
| Patient 3 | 7 | 0.18 | 0.06 | 0.10 | 0.04 | 1.5e-4 |
| Patient 4 | 6 | 0.17 | 0.07 | 0.13 | 0.03 | 0.02 |
| Patient 5 | 5 | 0.21 | 0.15 | 0.20 | 0.08 | 0.86 |

For regions with nearly uniform intensity, the deformation computed by the Demons method is entirely governed by the registration regularization terms, which do not need to be physically meaningful for the image-based method. Our method enforces physically-based constraints and results in errors within the diameter of the spot. Notice that for the Demons method, we replaced the voxel values inside the prostate with the average intensity within the organ, since the intensity and gradient information from the landmarks could also be utilized in the image-based registration, giving it an additional advantage, while our method is based purely on the physics-based simulation and does not take advantage of the landmarks.

E. Extension: Nonlinear FEM

To demonstrate that our optimization framework can also be applicable to nonlinear models, we incorporated a geometrically nonlinear FEM and the neo-Hookean model with the elasticity optimization scheme. The linearized equilibrium formulation of the nonlinear FEM is $$K(u^n) \cdot \Delta u = f^{ext} - f^{int} \quad (5)$$

where $f^{ext}$ and $f^{int}$ are the external and internal force vectors, $K(u^n)$ is the stiffness matrix that depends on the current displacement vector $u^n$, and $\Delta u$ is used to update the vector $u^n$ in a Newton iteration ($u^{n+1} = u^n + \Delta u$). The Jacobian matrix $$J_u = \left[ \frac{\partial u_i}{\partial E_j} \right]$$

(derivative of displacements u with respect to the elasticity parameter $E_j$) for the elasticity optimizer is approximated using the finite difference method due to the complexity of differentiating the internal forces with respect to the elasticity. Notice that we have not implemented force optimization for the nonlinear model, and boundary conditions given by a surface matching is always used in the simulation.

1) Synthetic Scene with Multiple Organs:

We used the same multi-organ scenes in Section III-A and deformed them using the nonlinear FEM to generate the synthetic target surfaces. That is, the nonlinear FEM is used in both generating synthetic cases and in the optimization scheme. The resulting recovered elasticity values are shown in Table VI. The errors are within 13% for the range we tested (50-200 kPa).

TABLE VI

| | | True Elasticity (kPA) | | | |
|---|---|---|---|---|---|
| | | 50 | 100 | 150 | 200 |
| Scene 1 | Recovered Value | 50.18 | 105.64 | 159.00 | 174.00 |
| | Relative Error | +0.35% | +5.6% | +6% | −13% |
| Scene 2 | Recovered Value | 45 | 105 | 141.5 | 197 |
| | Relative Error | −10% | +5% | −5.67% | −1.5% |

2) Assessment of Prostate Cancer Stage:

We repeated the experiments in Section III-B using the nonlinear FEM. The recovered elasticity values for the 10 patient data sets are shown in Table VII.

TABLE VII

| | Average Young's Modulus (kPa) | Std. Deviation | Clinical T-Stage |
|---|---|---|---|
| Patient 1 | 47.29 | 3.25 | T1 |
| Patient 2 | 69.28 | 8.09 | T3 |
| Patient 3 | 78.91 | 4.81 | T3 |
| Patient 4 | 63.62 | 2.92 | T2 |
| Patient 5 | 47.45 | 16.62 | T1 |
| Patient 6 | 59.85 | 18.37 | T1 |
| Patient 7 | 62.73 | 18.34 | T2 |
| Patient 8 | 60.23 | 11.93 | T2 |
| Patient 9 | 69.74 | 11.46 | T1 |
| Patient 10 | 69.25 | 17.64 | T2 |

Figure 13:
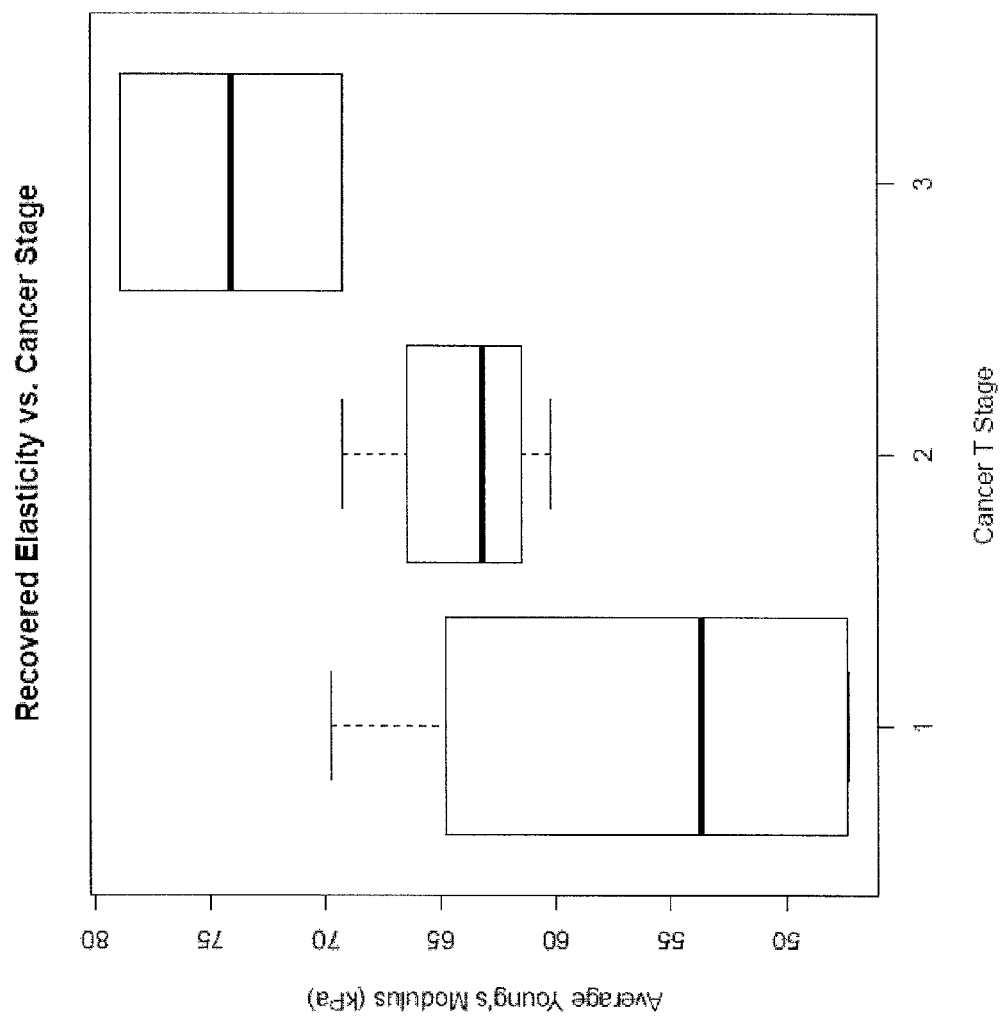
FIG. 13 is a box plot of average recovered elasticity versus cancer stage.

FIG. 13 shows a box plot of the average recovered elasticity and clinical T-stage. The Pearson (linear) correlation coefficient for recovered elasticity values and T-stages is 0.704 with a p-value of 0.023, and the Spearman's rank correlation p is 0.636 with a p-value of 0.048, which again shows a significant positive correlation between the stiffness value and the cancer stage for this group of patients. However, the recovered values are less consistent than those from the linear FEM implementation. We conjecture that the implementation using nonlinear FEM is more sensitive to the material properties and boundary conditions, and therefore the recovered values vary more than those using the linear FEM.

IV. ACCELERATION USING REDUCED-DIMENSION MODELING

The iterative optimization scheme requires a large number of solutions of the global linear system provided by the FEM. While the performance is acceptable for simple models with low degrees of freedom, it may take more than eight hours for some complex 3D models with many thousands of degrees of freedom for boundary forces. Here we present an acceleration method that reduces the dimensionality of the parameter space (the boundary forces) and thus improves the convergence of the optimizer.

Krysl et al (2001) [51] suggested that the FE model could be simplified with a set of basis vectors for the displacement field. The reduced-dimension displacement vector $\hat{u}$ is computed with $$u = W\hat{u} \quad (6)$$

where W is the column matrix of orthonormal basis vectors called the reduced basis. Substituting Equation 4 into Equation 1 and left-multiply both sides with $W^T$, we have the reduced-dimension linear system $$W^T K W \hat{u} = W^T f$$

$$\hat{K} \hat{u} = \hat{f} \quad (7)$$

where $\hat{K} = W^T K W$ and $\hat{f} = W^T f$.

In order to obtain W, a set of example displacements is used in a principal component analysis (PCA), and some of the resulting principal components serve as the basis vectors. However, the generation of the example displacements is nontrivial and depends on the specifics of the application. In keyframe-based animation, for instance, the keyframes can serve as the examples [44].

In medical image analysis, there can be multiple 3D images of each patient taken on different days. Once the organs in the images are delineated, they can provide examples of organ deformations. Furthermore, if images from different patients can all be used as example deformations, the resulting basis vectors can more effectively represent the general set of displacements, even for surfaces that are not used in the training process. In order to achieve this, a one-to-one correspondence must exist between boundary nodes in each pair of FE models, and only the degrees of freedom for these boundary nodes can be reduced (and other degrees of freedom are not affected by W).

We have implemented the elasticity parameter estimation algorithm and the acceleration techniques introduced here. We have applied our method to 2D shape deformations and a 3D elastography example using the reduced-dimension modeling.

A. Physically-Based 2D Shape Deformation

In 2D shape deformation with a single material, the elasticity (Young's modulus) cannot be estimated, since we do not know the true force applied. On the other hand, the compressibility (Poisson's ratio) is the main source of difference in deformed shape, if the same first-type boundary conditions are applied. A perfectly incompressible material has the value 0.5 (but in the isotropic linear elasticity model, the value cannot be exactly 0.5). Given the source piecewise linear (represented by vertices and edges) shape, we build the triangular finite element mesh that fills the shape using the library Triangle [57]. The target shape is also given in the piecewise linear format, and the distance function between the two shapes is based on distance between corresponding vertices. The boundary forces to be optimized are applied to a subset of nodes, which can be chosen by the user. The FE mesh and the recovered Poisson's ratio can be used to generate other deformations of the same object.

3D Elastography Using Reduced Modeling

Referring again to FIG. 4, which shows a finite element model of a domain that consists of the bladder, the prostate, the rectum, and the bones, our framework is applied to 3D elastography of the prostate. The space is filled with tetrahedral elements using the library TetGen [39], and the bladder and the rectum are hollow to reflect their structure, as shown in FIG. 4. There are two material properties, one assigned to the prostate (red elements in FIG. 4), and the other assigned to the elements between organs (shown in green in FIG. 4). The goal of the elastography is to find the ratio of Young's moduli of the prostate to that of the other elements. (The bone is always fixed, so its material property is irrelevant.) The Young's modulus is the material property to be optimized here because of its significance in noninvasive cancer detection. Poisson's ratios are set to 0.4 and 0.35 for the two materials, based on common values used in medical simulations [30]. Boundary forces are applied to the surface nodes of the bladder and the rectum. The parameters to be optimized are the Young's modulus of the prostate and the boundary forces applied to the bladder and the rectum.

Reduced basis training. The degrees of freedom for the boundary forces are around 4,900, which makes the optimizer slow to converge (taking thousands of iterations). Therefore, a dimension reduction is performed with 108 example deformations from CT images. These images are from nine patient data sets, each has one source image and several target images. The first step of generating examples is to create the node-to-node correspondence between source surfaces from different (patient) data sets. We use a surface matching approach to establish the correspondence: an atlas surface is iteratively deformed to match each patient-specific source surface, and therefore each patient-specific surface has the same set of nodes. The patient-specific source surface is then matched with corresponding target surfaces to generate the example deformations for the organ.

FIG. 14 shows plots of percentage of variance explained versus the number of principal components for the bladder and the rectum. We choose to use 92 basis vectors (principal components) for the bladder and 100 for the rectum due to the high accuracy requirement in elasticity parameter estimation.

We then test the accuracy of estimated elasticity values using two patient-specific FE models that are not used in the training process. The models are deformed using three different elasticity values to generate the target surfaces, so that we know the ground truth for the optimization. The relative errors range from 0.1% up to 8.1% and are generally less than 10% for the set of basis vectors chosen. The optimizer takes around 100-200 iterations to converge—in an amount of time that is about ⅟30 of what would otherwise be needed when using a full FE model. The average time needed for each iteration of force optimization is about 9 seconds.

V. CONCLUSION

We have presented a novel physically-based method for simultaneously estimating the 3D deformation of soft bodies and determining the unknown material properties and boundary conditions. Previous elastography methods are limited by imaging modalities and force measurement schemes, and we overcome these limitations by utilizing the surface information extracted from 3D images. Although the resolution of the resulting elastogram is limited to the object boundaries, we showed that the recovered value reflects the distribution of materials within the object, and the recovered elasticity values have a significant positive correlation with clinical prostate cancer staging in small-scale experiments. Therefore, our method has the potential to become a means of noninvasive cancer detection.

As a non-rigid image registration method, ours automatically determines the patient-specific material properties during the registration. The resulting deformation field is enforced to be physically plausible, since it is computed by the 3D FEM simulator with appropriate contact constraints among organs. The observed error on the boundary is within the resolution of the segmented images, and the error on the internal bright spots as landmarks in the prostate is comparable to the diameter of the spots.

The optimization framework for joint estimation of both 3D deformation and material parameters is generalizable. It is not limited to elasticity reconstruction and could be used for more sophisticated physiological models than the basic linear and nonlinear elasticity models we chose for simplicity in our current implementation. As an image registration technique, our method is reliable in terms of the registration error; as a parameter estimation method, our system can save an enormous amount of efforts adjusting the simulation parameters manually by automatically extracting patient-specific tissue properties. Furthermore, since only the 3D surfaces are used in our algorithm, applications other than medical image analysis could also adopt the method.

It will be understood that various details of the subject matter described herein may be changed without departing from the scope of the subject matter described herein. Furthermore, the foregoing description is for the purpose of illustration only, and not for the purpose of limitation.

REFERENCES

[1] M. Kauer, V. Vuskovic, J. Dual, G. Szekely, and M. Bajka, "Inverse finite element characterization of soft tissues," Medical Image Analysis, vol. 6, pp. 275-287, September 2002.

[2] C. Syllebranque and S. Boivin, "Estimation of mechanical parameters of deformable solids from videos," The Visual Computer, vol. 24, no. 11, pp. 963-972, 2008.

[3] J. Ophir, S. Alam, B. Garra, F Kallel, E. Konofagou, E L Krouskop, and T. Varghese, "Elastography: ultrasonic estimation and imaging of the elastic properties of tissues," Proceedings of the Institution of Mechanical Engineers, Part H: Journal of Engineering in Medicine, vol. 213, pp. 203-233, January 1999.

[4] A. Manduca, T. E. Oliphant, M. A. Dresner, J. L. Mahowald, S. A. Kruse, E. Amromin, J. P. Felmlee, J. F Greenleaf, and R. L. Ehman, "Magnetic resonance elastography: Non-invasive mapping of tissue elasticity," Medical Image Analysis, vol. 5, pp. 237-254, December 2001.

[5] 0. C. Zienkiewicz and R. L. Taylor, The Finite Element Method. Butterworth-Heinemann, Oxford, 6 ed., December 2005.

[6] A. Skovoroda and S. Emelianov, "Tissue elasticity reconstruction based on ultrasonic displacement and strain images," IEEE Transactions on Ultrasonics, Ferroelectrics, and Frequency Control, vol. 42, no. 4, p. 141, 1995.

[7] J. E. Lindop, G. M. Treece, A. H. Gee, and R. W. Prager, "3D elastography using freehand ultrasound," Ultrasound in Medicine & Biology, vol. 32, pp. 529-545, April 2006.

[8] H. Rivaz, E. Boctor, P. Foroughi, R. Zellars, G. Fichtinger, and G. Hager, "Ultrasound elastography: A dynamic programming approach," Medical Imaging, IEEE Transactions on, vol. 27, no. 10, pp. 1373-1377, 2008.

[9] 5. E. Salcudean, D. French, S. Bachmann, R. Zahiri-Azar, X. Wen, and W. J. Morris, "Viscoelasticity modeling of the prostate region using vibroelastography," in Medical Image Computing and Computer-Assisted Intervention—MICCAI 2006, vol. 4190, pp. 3 89-396, Springer Berlin Heidelberg, 2006.

[10] Y. Zhu, T. Hall, and J. Jiang, "A finite-element approach for young's modulus reconstruction," Medical Imaging, IEEE Transactions on, vol. 22, no. 7, pp. 890-901, 2003.

[11] M. Becker and M. Teschner, "Robust and efficient estimation of elasticity parameters using the linear finite element method," Proc. of Simulation and Visualization, pp. 15-28, 2007.

[12] H. Eskandari, S. E. Salcudean, R. Rohling, and I. Bell, "Real-time solution of the finite element inverse problem of viscoelasticity," Inverse Problems, vol. 27, p. 085002, August 2011.

[13] D. S. Schnur and N. Zabaras, "An inverse method for determining elastic material properties and a material interface," International Journal for Numerical Methods in Engineering, vol. 33, no. 10, pp. 2039-2057, 1992.

[14] F. Kallel and M. Bertrand, "Tissue elasticity reconstruction using linear perturbation method," Medical Imaging, IEEE Transactions on, vol. 15, no. 3, pp. 299-3 13, 1996.

[15] S. Balocco, O. Camara, and A. F Frangi, "Towards regional elastography of intracranial aneurysms," in Medical Image Computing and Computer-Assisted Intervention, vol. 11, pp. 13 1-8, 2008. PMID: 18982598.

[16] C. W. Washington and M. I. Miga, "Modality independent elastography (MIE): a new approach to elasticity imaging," IEEE Trans. on Medical Image, vol. 23, no. 9, pp. 1117-1 128, 2004.

[17] P. Courtis and A. Samani, "Detecting mechanical abnormalities in prostate tissue using FE-Based image registration," in MICCAI 2007 (N. Ayache, S. Ourselin, and A. Maeder, eds.), vol. 4792 of Lecture Notes in Computer Science, pp. 244-251, Springer Berlin I Heidelberg, 2007.

[18] L. Han, J. H. Hipwell, C. Tanner, Z. Taylor, T. Mertzanidou, J. Cardoso, S. Ourselin, and D. J. Hawkes, "Development of patient-specific biomechanical models for predicting large breast deformation," Physics in Medicine and Biology, vol. 57, pp. 455-472, January 2012.

[19] P. Risholm, E. Samset, and W. Wells, "Bayesian estimation of deformation and elastic parameters in non-rigid registration," Biomedical Image Registration, p. 104-115, 2010.

[20] V. Egorov, S. Ayrapetyan, and A. Sarvazyan, "Prostate mechanical imaging: 3-D image composition and feature calculations," Medical Imaging, IEEE Transactions on, vol. 25, pp. 1329-1340, October 2006.

[21] R. Chopra, A. Arani, Y. Huang, M. Musquera, J. Wachsmuth, M. Bronskill, and D. Plewes, "In vivo MR elastography of the prostate gland using a transurethral actuator," Magnetic Resonance in Medicine, vol. 62, no. 3, pp. 665-671, 2009.

[22] M. Sermesant, P. Moireau, O. Camara, J. Sainte-Marie, R. Andriantsimiavona, R. Cimrman, D. L. G. Hill, D. Chapelle, and R. Razavi, "Cardiac function estimation from MRI using a heart model and data assimilation: Advances and difficulties," Medical Image Analysis, vol. 10, no. 4, pp. 642-656, 2006.

[23] P. Moireau, D. Chapelle, and P. L. Tallec, "Joint state and parameter estimation for distributed mechanical systems," Computer Methods in Applied Mechanics and Engineering, vol. 197, pp. 659-677, January 2008.

[24] J. Maintz and M. A. Viergever, "A survey of medical image registration," Medical Image Analysis, vol. 2, pp. 1-36, March 1998.

[25] M. Holden, "A review of geometric transformations for nonrigid body registration," Medical Imaging, IEEE Transactions on, vol. 27, no. 1, pp. 111-128, 2008.

[26] M. Ferrant, S. K. Warfield, C. R. G. Guttmann, R. V. Mulkern, F A. Jolesz, and R. Kikinis, "3D image matching using a finite element based elastic deformation model," in MICCAI, pp. 202-209, 1999.

[27] M. Ferrant, S. K. Warfield, A. Nabavi, F A. Jolesz, and R. Kikinis, "Registration of 3D intraoperative MR images of the brain using a finite element biomechanical model," in MICCAI, pp. 19-28, 2000.

[28] A. Bharatha, M. Hirose, N. Hata, S. K. Warfield, M. Ferrant, K. H. Zou, E. Suarez-Santana, J. Ruiz-Alzola, A. D'Amico, R. A. Cormack, R. Kikinis, F A. Jolesz, and C. M. C. Tempany, "Evaluation of three-dimensional finite element-based deformable registration of pre- and intraoperative prostate imaging," Medical Physics, vol. 28, no. 12, p. 2551, 2001.

[29] D. Cash, M. Miga, T. Sinha, R. Galloway, and W. Chapman, "Compensating for intraoperative soft-tissue deformations using incomplete surface data and finite elements," Medical Imaging, IEEE Transactions on, vol. 24, pp. 1479-1491, November 2005.

[30] J. M. Hensel, C. Menard, P. W. M. Chung, M. F Milosevic, A. Kirilova, J. L. Moseley, M. A. Haider, and K. K. Brock, "Development of multiorgan finite element-based prostate deformation model enabling registration of endorectal coil magnetic resonance imaging for radiotherapy planning," mt. J. Radiation Oncology Bio. Phys., vol. 68, no. 5, pp. 1522-1528, 2007.

[31] A. Wittek, K. Miller, R. Kikinis, and S. K. Warfield, "Patient-specific model of brain deformation: Application to medical image registration," Journal of Biomechanics, vol. 40, no. 4, pp. 9 19-929, 2007.

[32] J. Crouch, S. Pizer, E. Chancy, Y. Hu, G. Mageras, and M. Zaider, "Automated Finite-Element analysis for deformable registration of prostate images," Medical Imaging, IEEE Transactions on, vol. 26, pp. 1379-1390, October 2007.

[33] R. Alterovitz, K. Goldberg, J. Pouliot, I. Hsu, Y. Kim, S. Noworolski, and J. Kurhanewicz, "Registration of MR prostate images with biomechanical modeling and nonlinear parameter estimation:' Medical Physics, vol. 33, p. 446, 2006.

[34] M. Foskey, B. Davis, L. Goyal, S. Chang, E. Chancy, N. Strehl, S. Tomei, J. Rosenman, and S. Joshi, "Large deformation Three-Dimensional image registration in Image-Guided radiation therapy:' Physics in Medicine and Biology, vol. 50, pp. 5869-5892, 2005.

[35] J. Nocedal and S. Wright, Numerical Optimization. Springer, 1999.

[36] T. A. Krouskop, T. M. Wheeler, F Kallel, B. S. Garra, and T. Hall, "Elastic moduli of breast and prostate tissues under compression," Ultrasonic imaging (Print), vol. 20, no. 4, pp. 260-274, 1998.

[37] C. Tanner, J. A. Schnabel, D. L. G. Hill, D. J. Hawkes, M. O. Leach, and D. R. Hose, "Factors influencing the accuracy of biomechanical breast models," Medical Physics, vol. 33, no. 6, p. 1758, 2006.

[38] P. A. Yushkevich, J. Piven, H. C. Hazlett, R. G. Smith, S. Ho, J. C. Gee, and G. Gerig, "User-guided 3D active contour segmentation of anatomical structures: Significantly improved efficiency and reliability," NeuroImage, vol. 31, pp. 1116-1128, July 2006.

[39] H. Si, "TetGen: a quality tetrahedral mesh generator and Three-Dimensional delaunay triangulator," December 2009.

[40] T. S. Yoo, M. J. Ackerman, W. E. Lorensen, W. Schroeder, V. Chalana, S. Aylward, D. Metaxas, and R. Whitaker, "Engineering and algorithm design for an image processing API: a technical report on ITK—the insight toolkit," 2002.

[41] 5. Balay, W. D. Gropp, L. C. McInnes, and B. F Smith, "Efficient management of parallelism in Object-Oriented numerical software libraries," Modem Software Tools in Scientific Computing, pp. 163-202, 1997.

[42] L. H. Sobin, TNM Classification of Malignant Tumours. John Wiley and Sons, December 2009.

[43] J. Thirion, "Image matching as a diffusion process: an analogy with maxwell's demons," Medical Image Analysis, vol. 2, no. 3, pp. 243-260, 1998.

[44] J. Barbic, M. da Silva, J. Popovic (2009) Deformable object animation using reduced optimal control. ACM Transactions on Graphics—Preceedings of ACM SIGGRAPH 2009 28(3):1, DOT 10.1145/1531326. 1531359, URL http://portal.acm.org/citation.cfm?doid=1531326.1531359

[45] M. Bergou, S. Mathur, M. Wardetzky, E. Grinspun (2007) TRACKS: toward directable thin shells. In: ACM STGGRAPH 2007 papers, ACM, San Diego, Calif., p 50, URL http://portal.acm.org/citation.cfm?id=1275808.1276439&coll=portal&dl=ACM&CFID=92920094&CFTOKEN=78895682

[46] K. S. Bhat, C. D. Twigg, J. K. Hodgins, P. K. Khosla, Z. Popovic, S. M. Seitz (2003) Estimating cloth simulation parameters from video. In: Proceedings of the 2003 ACM STGGRAPH/Eurographics symposium on Computer animation, Eurographics Association Aire-la-Ville, Switzerland, pp 37-51

[47] B. Bickel, M. Bächer, M. A. Otaduy, W. Matusik, H. Pfister, M. Gross (2009) Capture and modeling of nonlinear heterogeneous soft tissue. In: ACM STGGRAPH 2009 papers, ACM, New Orleans, La., pp 1-9, DOT 10.1145/1576246.1531395, URL http://portal.acm.org/citation.cfm?id=1531395

[48] B. Bickel, M. Bächer, M. A. Otaduy, H. R. Lee, H. Pfister, M. Gross, W. Matusik (2010) Design and fabrication of materials with desired deformation behavior. In: ACM STGGRAPH 2010 papers, ACM, Los Angeles, Calif., pp 1-10, DOT 10.1145/1833349.1778800, URL http://portal.acm.org/citation.cfm?id=1833349.1778800&coll=GUIDE&dl=GUIDE&CFID=107466681&CFTOKEN=52303178

[49] D. Fu, S. Levinson, S. Gracewski, K. Parker (2000) Non-invasive quantitative reconstruction of tissue elasticity using an iterative forward approach. PHYSICS IN MEDICINE AND BIOLOGY 45(6):1495-1510

[50] T. Tgarashi, T. Moscovich, J. F. Hughes (2005) As-rigid-as-possible shape manipulation. ACM Trans Graph 24(3): 1134-1141, DOT 10.1145/1073204.1073323, URL http://doi.acm.org/1O.1145/1O72O4.1073323

[51] P. Krysl, S. Lall, J. E. Marsden (2001) Dimensional model reduction in non-linear finite element dynamics of solids and structures. International Journal for Numerical Methods in Engineering 51(4):479-504, DOT 10.1002/nme. 167, URL http://onlinelibrary.wiley.com/doi/10.1002/rune.167/abstract

[52] H. Lee, M. Foskey, M. Niethammer, M. Lin M (2010) Physically-based deformable image registration with material property and boundary condition estimation. In: Proceedings of the 2010 TEEE international conference on Biomedical imaging: from nano to Macro, TEEE Press, Rotterdam, Netherlands, pp 532-535, URL http://portal.acm.org/citation.cfm?id=1855963.1856099

[53] A. McNamara, A. Treuille, Z. Popovi, J. Stam (2004) Fluid control using the adjoint method. ACM Trans Graph 23(3):449-456, URL http://portal.acm.org/citation.cfm?id=1015706.1015744

[54] R. Muthupillai, R. L. Ehman (1996) Magnetic resonance elastography. Nat Med 2(5):601-603, DOT 10.1038/nm0596-601, URL http://dx.doi.org/I0.1038/run0596-601

[55] A. Nealen, M. Muller, R. Keiser, E. Boxerman, M. Carlson (2006) Physically based deformable models in computer graphics. Tn: Computer Graphics Forum, vol 25, pp 809-836

[56] J. Nocedal, S. Wright (1999) Numerical Optimization. Springer Ophir J, Alam 5, Garra B, Kallel F, Konofagou E, Krouskop T, Varghese T (1999) Elastography: ultrasonic estimation and imaging of the elastic properties of tissues. Proceedings of the Institution of Mechanical. Engineers, Part H: Journal of Engineering in Medicine 213(3):203-233, DOT 10.1243/0954411991534933, URL http://dx.doi.org/10.1243/0954411991534933 Press WH (2007) Numerical recipes. Cambridge University Press

[57] J. R. Shewchuk (1996) Triangle: Engineering a 2D quality mesh generator and delaunay triangulator. In: Applied Computational Geometry Towards Geometric Engineering, vol 1148, Springer-Verlag, Berlin/Heidelberg, pp 203-222, URL http://www.springerlink.com/content/w164563587465326/

[58] Z. A. Taylor, S. Crozier, S. Ourselin (2010) Realtime surgical simulation using reduced order finite element analysis. MTCCAT 2010 13(Pt 2):388-395, URL http://www.ncbi.nlm.nih.gov/pubmed/20879339, PMTD: 20879339

[59] M. Teschner, B. Heidelberger, D. Manocha, N. Govindaraju, G. Zachmann, S. Kimmerle, J. Mezger, A. Fuhrmann (2005) Collision handling in dynamic simulation environments: The evolution of graphics: Where to next? In: Eurographics 2005 Tutorial

[60] A. Treuille, A. McNamara, Z. Popovic, J. Stam (2003) Keyframe control of smoke simulations. In: ACM STGGRAPH 2003 Papers, ACM, San Diego, Calif., pp 716-723, URL http://portal.acm.org/citation.cfm?id=1201775.882337&coll=portal&dl=ACM&CFID=92920094&CFTOKEN=78895682

[61] Y. Weng, W. Xu, Y. Wu, K. Zhou, B. Guo (2006) 2D shape deformation using nonlinear least squares optimization. The Visual Computer 22(9-11):653-660, DOT IO.I007/s00371-006-0054-y, URL http://www.springerlink.com/content/8hwv2183455t232v/

[62] W. Yang, J. Feng, X. Jin (2008) Shape deformation with tunable stiffness. The Visual Computer 24(7-9):495-503, DOT 10.1007/s00371-008-0230-3, URL http://www.springerlink.com/content/q22t771352785451/

What is claimed is:

1. A method for simulation-based estimation of elasticity parameters, the method comprising:
   constructing a 3D model of an object comprising biological tissue, the model having a first shape and an elasticity value;
   simulating the application of an external force to a 3D model of an object comprising biological tissue, the model having a first shape and an elasticity value, the simulated external force having a force value and the application of the simulated force causing the model to deform to a second shape;
   measuring a difference between the second shape and a target shape;
   determining whether the measured difference between the second shape and the target shape is within a threshold of error;
   in response to a determination that the measured difference is not within the threshold of error, adjusting at least one of the elasticity value and the force value and repeating the simulating, measuring, and determining until the measured difference is within the threshold of error; and
   in response to a determination that the measured difference is within the threshold of error, mapping the elasticity value to a diagnostic parameter.

2. The method of claim 1 wherein the diagnostic parameter is a tissue elasticity value.

3. The method of claim 1 wherein the diagnostic parameter is an indication of a possibility of cancer, a presence of cancer, or a stage of cancer.

4. The method of claim 1 wherein the diagnostic parameter is an indication of the health of the object modeled.

5. The method of claim 1 wherein the first shape is determined from a first 3D image of the object and wherein the target shape is determined from a second 3D image of the object.

6. The method of claim 5 wherein the first and second 3D images are images of the same object from the same patient.

7. The method of claim 1 wherein the first shape or the target shape is determined from statistical analysis of the same object from multiple patients.

8. The method of claim 1 wherein the 3D model represents one or more organs, one or more tissues, or a combination of the above.

9. The method of claim 1 wherein constructing the 3D model of the object comprises constructing a finite element model of the object.

10. The method of claim 1 wherein constructing the 3D model includes performing data reduction on the finite element model of the object prior to the simulation step to reduce the number of elements being simulated.

11. The method of claim 10 wherein performing dimension reduction on the finite element model comprises using principal component analysis to identify degrees of freedom to be removed from the finite element model and removing from the model the degrees of freedom so identified.

12. A system for three dimensional estimation of elasticity parameters, the system comprising:
   a simulator configured to simulate the application of an external force to a 3D model of an object comprising biological tissue, the model having a first shape and an elasticity value, the simulated external force having a force value and the application of the simulated force causing the model to deform to a second shape; and
   a parameter estimation module configured to measure a difference between the second shape and a target shape, to determine whether the measured difference between the second shape and the target shape is within a threshold of error, in response to a determination that the measured difference is not within the threshold of error, to adjust at least one of the elasticity value and the force value and repeated the simulating, measuring, and determining until the measured difference is within the threshold of error, and, in response to a determination that the measured difference is within the threshold of error, to map the elasticity value to a diagnostic parameter.

13. A non-transitory computer readable medium having stored therein executable instructions that when executed by the processor of a computer control the computer to perform steps comprising:
   constructing a 3D model of an object comprising biological tissue, the model having a first shape and an elasticity value;
   simulating the application of an external force to a 3D model of an object comprising biological tissue, the model having a first shape and an elasticity value, the simulated external force having a force value and the application of the simulated force causing the model to deform to a second shape;
   measuring a difference between the second shape and a target shape;
   determining whether the measured difference between the second shape and the target shape is within a threshold of error;
   in response to a determination that the measured difference is not within the threshold of error, adjusting at least one of the elasticity value and the force value and repeating the simulating, measuring, and determining until the measured difference is within the threshold of error; and
   in response to a determination that the measured difference is within the threshold of error, mapping the elasticity value to a diagnostic parameter.

* * * * *

UNITED STATES PATENT AND TRADEMARK OFFICE
CERTIFICATE OF CORRECTION

PATENT NO. : 9,636,075 B2
APPLICATION NO. : 14/420239
DATED : May 2, 2017
INVENTOR(S) : Lee et al.

Page 1 of 1

It is certified that error appears in the above-identified patent and that said Letters Patent is hereby corrected as shown below:

In the Specification

Column 1, Lines 15-20:
Replace: "This invention was made with government support under Grant No. W911NF-06-1-0355 awarded by the U.S. Army Research Office and Grant No. R01 RR018615 awarded by the National Center for Research Resources and the National Cancer Institute. The U.S. Government has certain rights in the invention."
With: "This invention was made with government support under Grant Number W911NF-06-1-0355 awarded by the U.S. Army Research Office and Grant Number RR018615 awarded by the National Institutes of Health. The government has certain rights in the invention."

Signed and Sealed this
Twenty-second Day of May, 2018

Andrei Iancu
*Director of the United States Patent and Trademark Office*